(12) United States Patent
Cory et al.

(10) Patent No.: US 6,790,637 B1
(45) Date of Patent: Sep. 14, 2004

(54) MAMMALIAN GENE, BCL-W, BELONGS TO THE BCL-2 FAMILY OF APOPTOSIS-CONTROLLING GENES

(75) Inventors: Suzanne Cory, North Melbourne (AU); Jerry McKee Adams, North Melbourne (AU); Leonie M. Gibson, Moonee Ponds (AU); Shaun P. Holmgreen, Box Hill (AU)

(73) Assignee: Cerylid Pty., Ltd., Richmond (AU)

( * ) Notice: Subject to any disclaimer, the term of this patent is extended or adjusted under 35 U.S.C. 154(b) by 0 days.

(21) Appl. No.: 09/155,327

(22) PCT Filed: Mar. 27, 1997

(86) PCT No.: PCT/AU97/00199

§ 371 (c)(1),
(2), (4) Date: Mar. 29, 1999

(87) PCT Pub. No.: WO97/35971

PCT Pub. Date: Oct. 2, 1997

(30) Foreign Application Priority Data

Mar. 27, 1996 (AU) ............................................. PN8965

(51) Int. Cl.$^7$ ........................... C12P 21/06; C12N 5/00; C12N 15/00; C07H 21/04
(52) U.S. Cl. ................... 435/69.1; 435/320.1; 435/325; 435/455; 536/23.1; 536/23.5
(58) Field of Search ............................ 435/69.1, 320.1, 435/325, 455; 536/23.1, 23.5

(56) References Cited

U.S. PATENT DOCUMENTS 5,789,201 A * 8/1998 Guastella .................... 435/69.1

FOREIGN PATENT DOCUMENTS

| EP | 0 252 685 A2 | 1/1988 | ......... G01N/33/574 |
| WO | WO 95/00642 | 1/1995 | ........... C12N/15/12 |

OTHER PUBLICATIONS

Boise et al., Cell, 74:597–608, 1993.
Brand et al., Gene, 154:187–192, 1995.
Chittenden et al., The EMBO Journal, 14:5589–5596, 1995.
Farrow et al., Nature, 374:731–733, 1995.
Hockenbery et al., Proc. Natl. Acad. Sci. USA, 88:6961–6965, 1991.
Kiefer et al., Nature, 374:736–739, 1995.
Oltvai et al., Cell, 74:609–619, 1993.
Subramanian et al., Oncogene, 11:2403–2409.
Yin et al., Nature, 369:321–323, 1994.
Chittenden, T., et al. (1995) *Nature* 374:733–736.
Cruz–Reyes, J., et al. (1995) *Gene* 158:171–179.
Fang, W., et al. (1994) *Cloning of Mouse*:4388–4398.
Gibson, L., et al. (1996) *Oncogene* 13:665–675.

* cited by examiner

*Primary Examiner*—Jeffrey Fredman
*Assistant Examiner*—Sumesh Kaushal
(74) *Attorney, Agent, or Firm*—Scully, Scott, Murphy & Presser

(57) ABSTRACT

The present invention is broadly directed to therapeutic molecules capable of inter alia modulating apoptosis in mammalian cells. The therapeutic molecules of the present invention encompass genetic sequences and chemical entities capable of regulating expression of a novel mammalian gene belonging to the bcl-2 family and which promotes cell survival. The therapeutic molecules of the present invention may have further utility in delaying cell cycle entry. In addition, the present invention extends to chemical entities capable of modulating activity and function of the translation product of said novel gene of the bcl-2 family. The present invention also extends to the translation product of the novel gene of the bcl-2 family and its use in, for example, therapy, diagnosis, antibody generation and as a screening tool for therapeutic molecules capable of modulating physiological cell death or survival and/or modulating cell cycle entry.

4 Claims, 26 Drawing Sheets

```
                      A              S1
Bclw        MATPASTPDT  RALVADFVGY
Bclw-Rox    MATPASTPDT  RALVADFVGY Bclw        DEFETRFRRT  FSDLAAQLHV
Bclw-Rox    DEFETRFRRT  FSDLAAQLHV Bclw        VFGAALCAES  VNKEMEPLVG
Bclw-Rox    VFGAALCAES  VNKEMEPLVG Bclw        YGDGALEEAR  RLREGNWASV
Bclw-Rox    ARVREMEEEA  EKLKELQNEV Bclw-Rox    IYVGNVDYGA  TAEELEAHFH Bclw-Rox    ESVRTSLALD  ESLFRGRQIK Bclw-Rox    NSSRSRFYSG  FNSRPRGRIY
```

Figure 1:
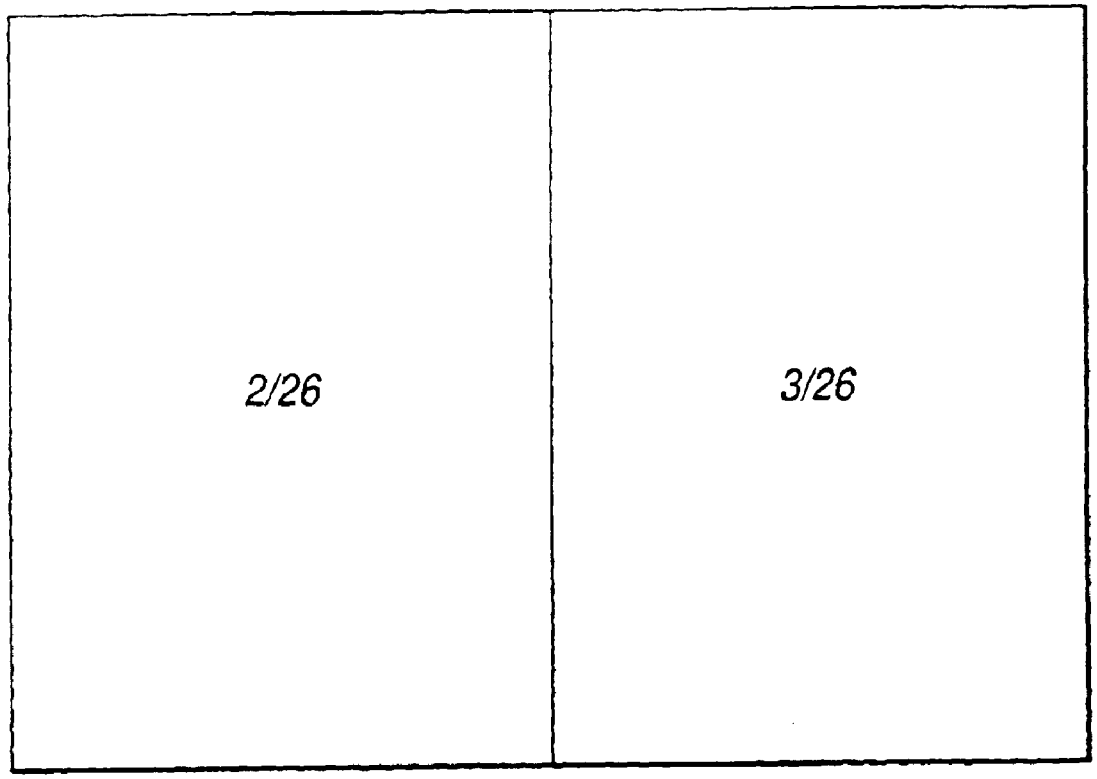

*Fig. 1 (i)*

```
KLRQKGY VCG   AGPGEGPAAD   PLHQAMRAAG    50
KLRQKGY VCG   AGPGEGPAAD   PLHQAMRAAG    50

S2
TPGSAQQR FT   QVSDELFQGG   PNWGRLVAFF   100
TPGSAQQR FT   QVSDELFQGG   PNWGRLVAFF   100

E                      S3
QVQDWMVAYL   ETRLAD WIHS   SGGWAEFTAL   150
QVQDWMVAYL   ETRLAD WIHS   SGGW ELEAIK  150
                              ▲

RTVLTGAVAL   GALVTVGAFF   ASK*          193
EKQMNMSPPP   GNAGPVIMSL   EEKMEADARS    200

GCGSVNRVTI   LCDKFSGHPK   GFAYIEFSDK    250

VIPKRTNRPG   ISTTDRGFPR   SRYRARTTNY    300

RGRARATSWY   SPY*                       333
```

Fig. 1 (ii)

```
                    S1
Bcl2    MAHAGRTGYD NREIVMKYIH YKLSQRGYEW
BclxL   ......MSQS NRELVVDFLS YKLSQKGYSW
Bclw    .MATPASAPD TRALVADFVG YKLRQKGYVC
Ced9              D IEGFVVDYFT HRIRQNGMEW Bak                                   MASG
Bax Bcl2    ASRDPVARTS PLQTPAAPGA AAGPAL....
BclxL   PSWH.LADSP AVNGATGHSS SLDARE....
Bclw    .......... .......... ..........
Ced9

Bak     FRSYVFYRHQ QEQEAEGVAA PADPEMVTLP
Bax     ....ALLLQG FIQDRAGRMG GEAPELALDP
Bik

S2
Bcl2    MSRQLHLTP FTARGRFATV VEELFRDG.V
BclxL   LTSQLHITP GTAYQSFEQV VNELFRDG.V
Bclw    LAAQLHVTP GSAQQRFTQV SDELFQGG.P
cED9    FCEQLLAVP RISFSLYQDV VRTVGNAQTD
```

Fig. 8 (i)

```
DAGDVGAAPP  GAAPAPGIFS  SQPGHTPHTA   60
SQFSDVEENR  TEAPEGTESE  METPSAINGN   54
GAGPGE....  ..........  ..........   35
                                     99

QGPGPPRQEC  GEPALPSASE  EQVAQDTEEV   34
  MDGSGEQPR  GGGPTSSEQI  MKTG......  23

BH3           NH1
                        ━━━━━━━━    ━━━━━━━
                        ▼     ▼
...SPVPPVV  HLTLRQAGDDFSRRYRRDFAE   113
...VIPMAAV  KQALREAGDEFELRYRRAFSD   107
...GPAADPL  HQAMRAAGDEFETRFRRTFSD    63
            HEMMRVMGTIFEKKHAENFET   132
              *     *

LQPSSTMGQV  GRQLAIIGDDINRRYDSEFQT    95
VPQDASTKKL  SECLKRIGDELDS..NMELQR    78
            LACIGDEMD
               △                       △
BH1
━━━━━
      *                        ▼▼▼  ▼
....NWGRIV  AFFEFGG..V  .MCVESVNRE   165
....NWGRIV  AFFSFGG..A  .LCVESVDKE   158
....NWGRLV  AFFVFGA..A  .LCAESVNKE   114
QCPMSYGRLI  GLISFGGFVA  AKMMESV..E   190
```

Figure 8:
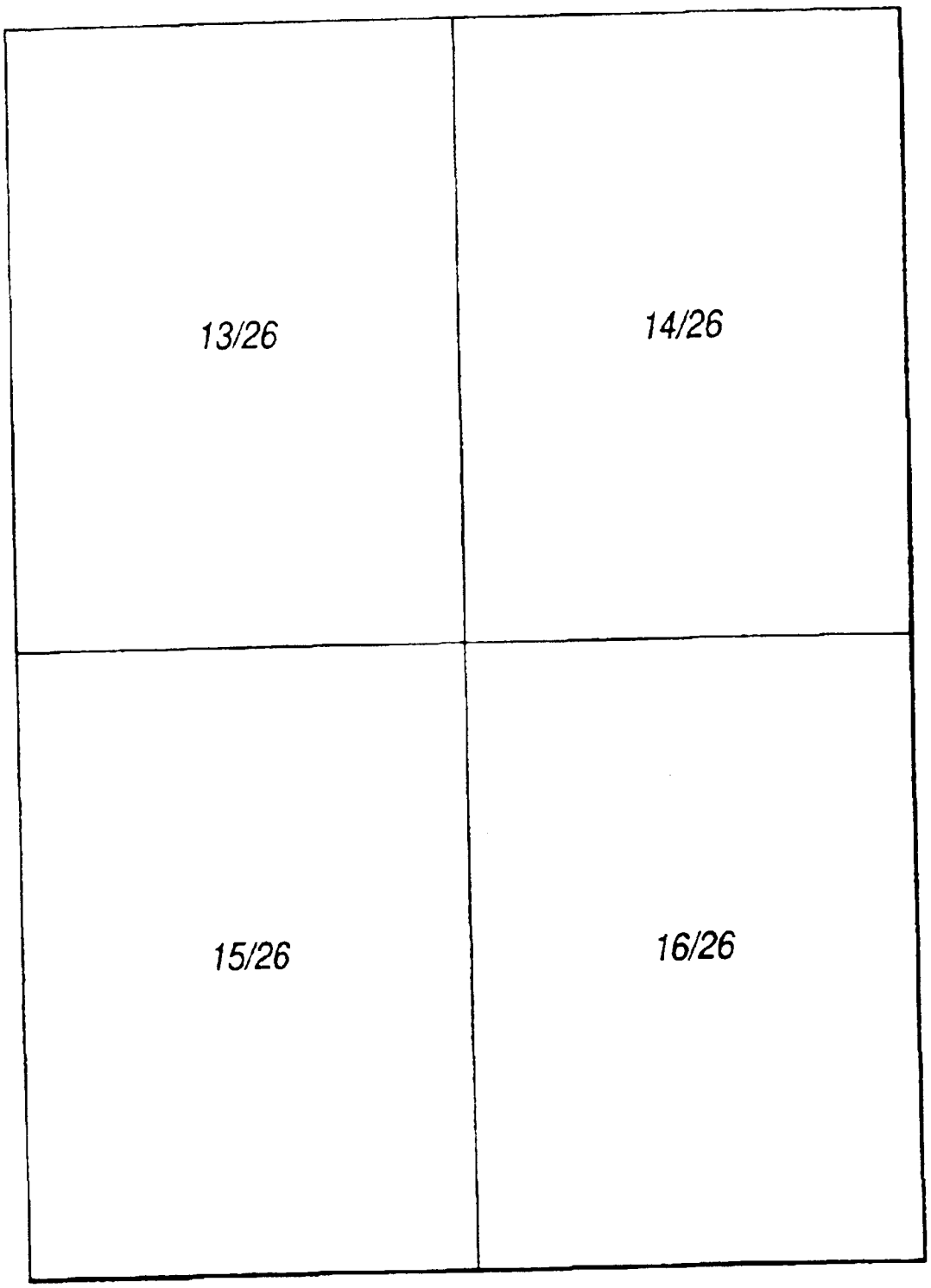

*Fig. 8 (ii)*

```
Bak     MLQHLQPTA  ENAYEYETKI  ATSLFESG.I
Bax     MIAAVD..T  DSPREVFFRV  AADMFSDGNF
               △       △  △    △
```

```
                                        S3
                                   *
Bc12    MSPLVDNIAL  WMTEYLNRH.  LHTWIQDNGG
BclxL   MQVLVSRIAA  WMATYLNDH.  LEPWIQENGG
Bclw    MEPLVGQVQE  WMVAYLETR.  LADWIHSSGG
Ced9    LQGQVRNLFV  YTSLFIKTRI  RNNWKEHNRS Bak     LTGFLGQVTR  FVVDFMLHHC  IARWIAQRGG
Bax     VPELIRTIMG  WTLDFLRERL  LG.WIQDQGG
                       △
```

```
                                ~~~~~~~~~~~
Bc12    DFSWLSLKTL  LSLAL.VGAC  ITLGAYLGHK
BclxL   RKGQERFNRW  FLTGMTVAGV  VLLGSLFSRK
Bclw    EGNWASVRTV  LTGAVALGAL  VTVGAFFASK Bak     .......GP   ILNVLVVLGV  VLLGQFVVRR
Bax     .......TPT  WQTVTIFVAG  VLTASLTIWK
```

Fig. 8 (iii)

```
....NWGRVV ALLGEGY..R .LALHVYQHG      146
....NWGRVV ALEYFAS..K .LVLKALCTK      128
                    Δ
```

BH2

```
WDAFVELYG. ...PSMRPLF                 210
WDTFVELYG. ...NNAAAES                 203
WAEFTALYGD GALEEARRLR                 163
WDDFMTL.G.                            218

WVAALNLGN. ..........                 185
WDGLLSYFG. ..........                 166

239
                                      233
                                      193

FFKS                                  211
KMG                                   192
```

Fig. 8 (iv)

| | | | | | | | |
|---|---|---|---|---|---|---|---|
| ATG | GCG | ACC | CCA | GCC | TCG | GCC | CCA | GAC |
| Met | Ala | Thr | Pro | Ala | Ser | Ala | Pro | Asp |
| 1 | | | | 5 | | | | |

| TTT | GTA | GGT | TAT | AAG | CTG | AGG | CAG | AAG |
|---|---|---|---|---|---|---|---|---|
| Phe | Val | Gly | Tyr | Lys | Leu | Arg | Gln | Lys |
| | | | 20 | | | | | 25 |

| CCC | GGG | GAG | GGC | CCA | GCA | GCT | GAC | CCG |
|---|---|---|---|---|---|---|---|---|
| Pro | Gly | Glu | Gly | Pro | Ala | Ala | Asp | Pro |
| | | 35 | | | | | 40 | |

| GCT | GGA | GAT | GAG | TTC | GAG | ACC | CGC | TTC |
|---|---|---|---|---|---|---|---|---|
| Ala | Gly | Asp | Glu | Phe | Glu | Thr | Arg | Phe |
| | | 50 | | | | 55 | | |

| GCG | GCT | CAG | CTG | CAT | GTG | ACC | CCA | GGC |
|---|---|---|---|---|---|---|---|---|
| Ala | Ala | Gln | Leu | His | Val | Thr | Pro | Gly |
| 65 | | | | | 70 | | | |

| CAG | GTC | TCC | GAC | GAA | CTT | TTT | CAA | GGG |
|---|---|---|---|---|---|---|---|---|
| Gln | Val | Ser | Asp | Glu | Leu | Phe | Gln | Gly |
| | | | | 85 | | | | |

| GTA | GCC | TTC | TTT | CTC | TTT | GGG | GCT | GCA |
|---|---|---|---|---|---|---|---|---|
| Val | Ala | Phe | Phe | Leu | Phe | Gly | Ala | Ala |
| | | | 100 | | | | | 105 |

Fig. 9A (i)

| | | | | | | | |
|---|---|---|---|---|---|---|---|
| ACA | CGG | GCT | CTG | GTG | GCA | GAC | 48 |
| Thr | Arg | Ala | Leu | Val | Ala | Asp | |
| 10 | | | | | 15 | | |
| | | | | | | | |
| GGT | TAT | GTC | TGT | GGA | GCT | GGC | 96 |
| Gly | Tyr | Val | Cys | Gly | Ala | Gly | |
| | | | | 30 | | | |
| | | | | | | | |
| CTG | CAC | CAA | GCC | ATG | CGG | GCA | 144 |
| Leu | His | Gln | Ala | Met | Arg | Ala | |
| | | | 45 | | | | |
| | | | | | | | |
| CGG | CGC | ACC | TTC | TCT | GAT | CTG | 192 |
| Arg | Arg | Thr | Phe | Ser | Asp | Leu | |
| | | 60 | | | | | |
| | | | | | | | |
| TCA | GCC | CAG | CAA | CGC | TTC | ACC | 240 |
| Ser | Ala | Gln | Gln | Arg | Phe | Thr | |
| | 75 | | | | | 80 | |
| | | | | | | | |
| GGC | CCC | AAC | TGG | GGC | CGC | CTT | 288 |
| Gly | Pro | Asn | Trp | Gly | Arg | Leu | |
| 90 | | | | | 95 | | |
| | | | | | | | |
| CTG | TGT | GCT | GAG | AGT | GTA | AAC | 336 |
| Leu | Cys | Ala | Glu | Ser | Val | Asn | |
| | | | | 110 | | | |

Fig. 9A (ii)

```
AAG GAG ATG GAA CCA CTG GTG GGA CAA
Lys Glu Met Glu Pro Leu Val Gly Gln
        115             120

TAC CTG GAG ACG CGG CTG GTC GAC TGG
Tyr Leu Glu Thr Arg Leu Val Asp Trp
    130                 135

GCG GAG TTC ACA GCT CTA TAC GGG GAC
Ala Glu Phe Thr Ala Leu Tyr Gly Asp
145                 150

CGT CTG CGG GAG GGG AAC TGG GCA TCA
Arg Leu Arg Glu Gly Asn Trp Ala Ser
                165

GCC GTG GCA CTG GGG GCC CTG GTA ACT
Ala Val Ala Leu Gly Ala Leu Val Thr
            180                 185

AAG TGA A
Lys  *
```

Fig. 9A (iii)

| | | | | | | | |
|---|---|---|---|---|---|---|---|
| GTG | CAG | GAG | TGG | ATG | GTG | GCC | 384 |
| Val | Gln | Glu | Trp | Met | Val | Ala | |
| | | | 125 | | | | |
| ATC | CAC | AGC | AGT | GGG | GGC | TGG | 432 |
| Ile | His | Ser | Ser | Gly | Gly | Trp | |
| | | | 140 | | | | |
| GGG | GCC | CTG | GAG | GAG | GCG | CGG | 480 |
| Gly | Ala | Leu | Glu | Glu | Ala | Arg | |
| | 155 | | | | | 160 | |
| GTG | AGG | ACA | GTG | CTG | ACG | GGG | 528 |
| Val | Arg | Thr | Val | Leu | Thr | Gly | |
| 170 | | | | 175 | | | |
| GTA | GGG | GCC | TTT | TTT | GCT | AGC | 576 |
| Val | Gly | Ala | Phe | Phe | Ala | Ser | |
| | | | | 190 | | | |
| | | | | | | | 583 |

Figure 9A:
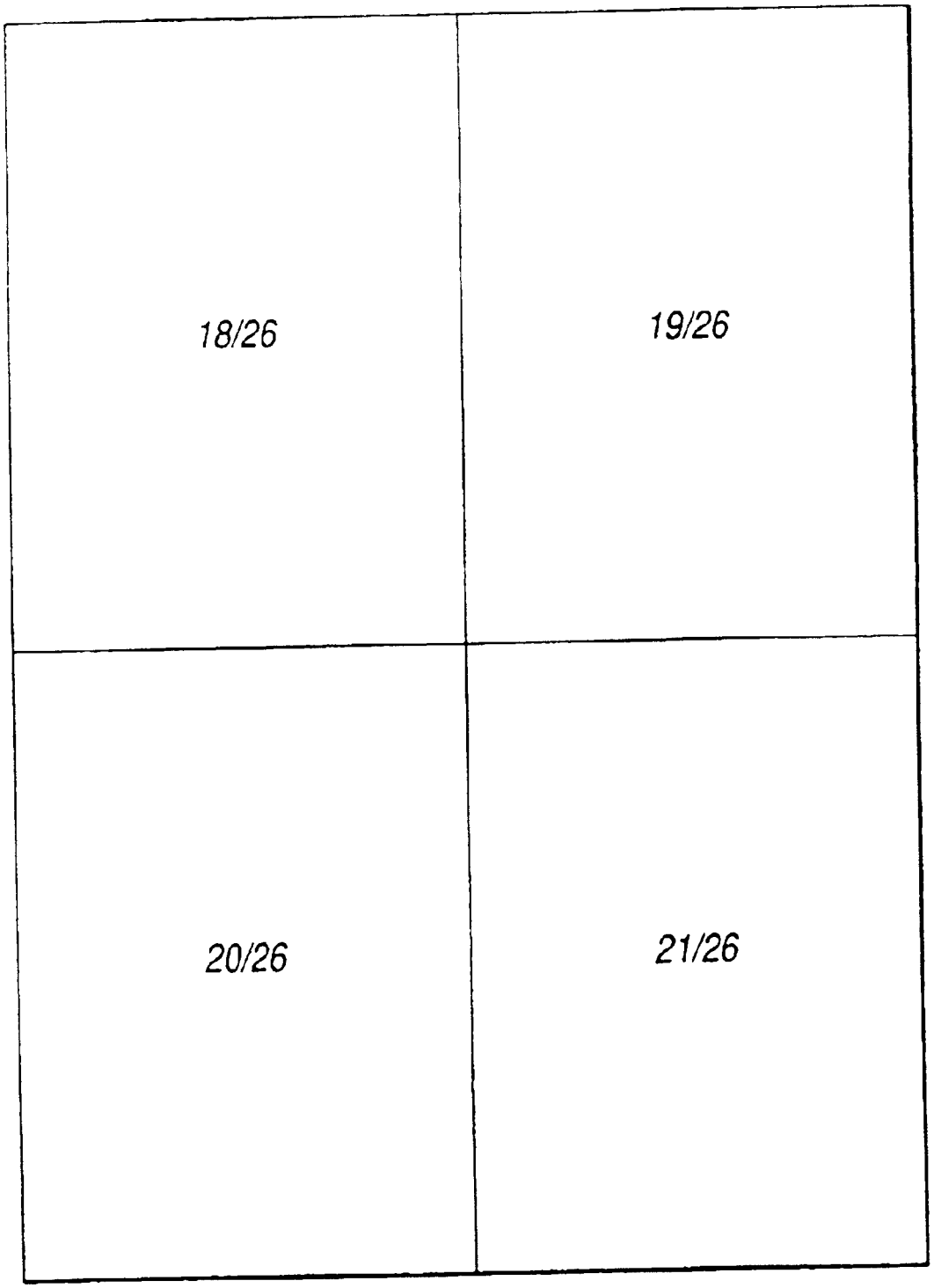

*Fig. 9A (iv)*

```
ATG CCG ACC CCA GCC TCA ACC CCA GAC
Met Pro Thr Pro Ala Ser Thr Pro Asp
 1               5

TTT GTA GGC TAT AGG CTG AGG CAG AAG
Phe Val Gly Tyr Arg Leu Arg Gln Lys
                 20               25

CCT GGG GAA GGC CCA GCC GCC GAC CCG
Pro Gly Glu Gly Pro Ala Ala Asp Pro
         35                   40

GCT GGA GAC GAG TTT GAG ACC CGT TTC
Ala Gly Asp Glu Phe Glu Thr Arg Phe
         50                   55

GCC GCT CAG CTG CAC GTG ACC CCA GGC
Ala Ala Gln Leu His Val Thr Pro Gly
 65                   70

CAG GTT TCC GAC GAA CTT TTC CAA GGG
Gln Val Ser Asp Glu Leu Phe Gln Gly
                 85

GTG GCA TTC TTT GTC TTT GGG GCT GCC
Val Ala Phe Phe Val Phe Gly Ala Ala
                100              105
```

Fig. 9B (i)

| | | | | | | | |
|---|---|---|---|---|---|---|---|
| ACA | CGC | GCT | CTA | GTG | GCT | GAC | 48 |
| Thr | Arg | Ala | Leu | Val | Ala | Asp | |
| 10 | | | | 15 | | | |

| | | | | | | | |
|---|---|---|---|---|---|---|---|
| GGT | TAT | GTC | TGT | GGA | GCT | GGG | 96 |
| Gly | Tyr | Val | Cys | Gly | Ala | Gly | |
| | | | | 30 | | | |

| | | | | | | | |
|---|---|---|---|---|---|---|---|
| CTG | CAC | CAA | GCC | ATG | CGG | GCT | 144 |
| Leu | His | Gln | Ala | Met | Arg | Ala | |
| | | | 45 | | | | |

| | | | | | | | |
|---|---|---|---|---|---|---|---|
| CGC | CGC | ACC | TTC | TCT | GAC | CTG | 192 |
| Arg | Arg | Thr | Phe | Ser | Asp | Leu | |
| | | 60 | | | | | |

| | | | | | | | |
|---|---|---|---|---|---|---|---|
| TCA | GCC | CAG | CAA | CGC | TTC | ACC | 240 |
| Ser | Ala | Gln | Gln | Arg | Phe | Thr | |
| 75 | | | | | | 80 | |

| | | | | | | | |
|---|---|---|---|---|---|---|---|
| GGC | CCT | AAC | TGG | GGC | CGT | CTT | 288 |
| Gly | Pro | Asn | Trp | Gly | Arg | Leu | |
| 90 | | | | | 95 | | |

| | | | | | | | |
|---|---|---|---|---|---|---|---|
| CTG | TGT | GCT | GAG | AGT | GTC | AAC | 336 |
| Leu | Cys | Ala | Glu | Ser | Val | Asn | |
| | | | | 110 | | | |

Figure 9B:
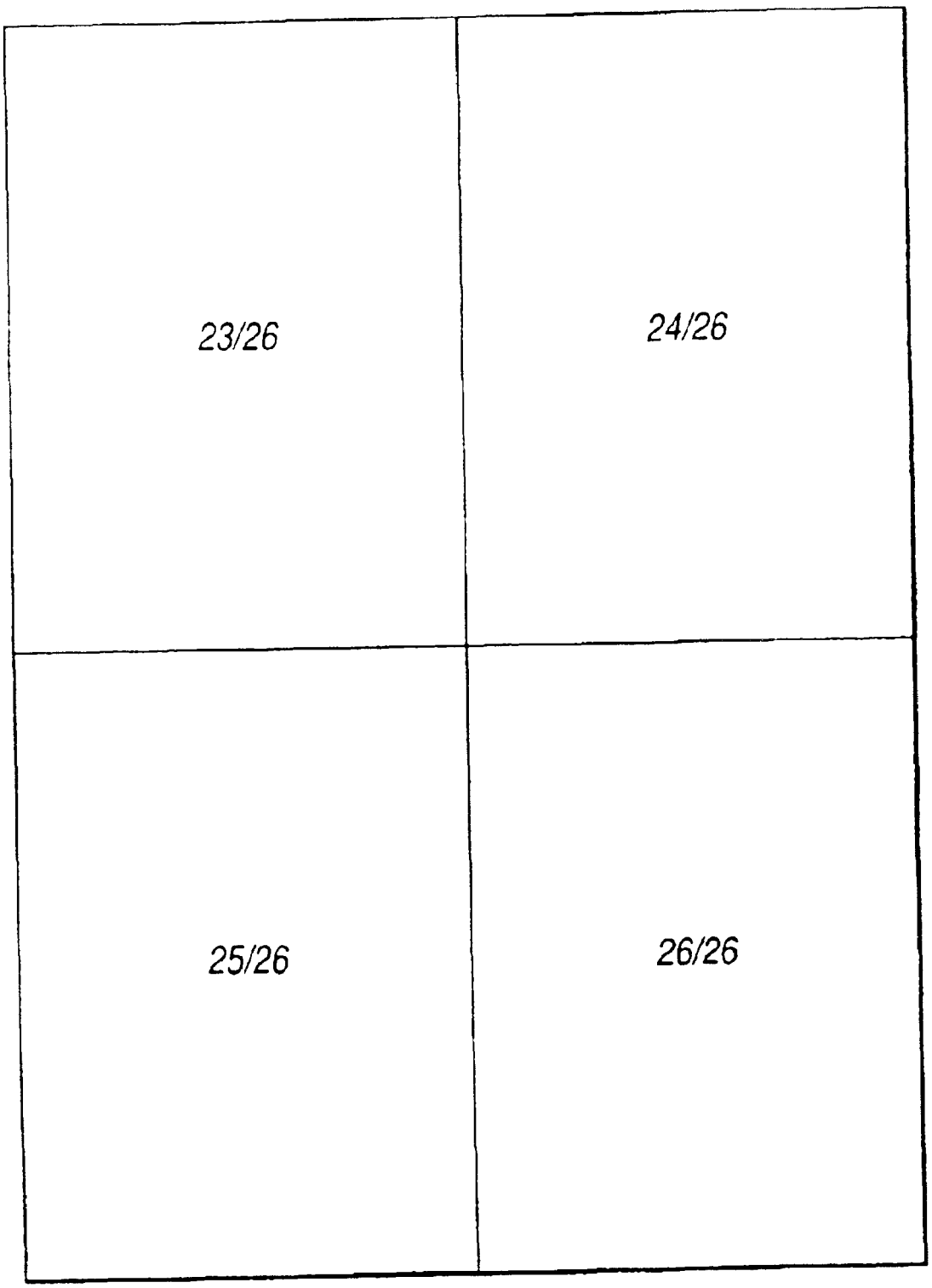

*Fig. 9B (ii)*

```
AAA GAA ATG GAG CCT TTG GTG GGA CAA
Lys Glu Met Glu Pro Leu Val Gly Gln
        115                 120

TAC CTG GAG ACA CGT CTG GTC GAC TGG
Tyr Leu Glu Thr Arg Leu Ala Asp Trp
    130                 135

GCG GAC TTC ACA GCT CTA TAC GGG GAC
Ala Asp Phe Thr Ala Leu Tyr Gly Asp
145                 150

CGT CTG CGG GAG GGC AAC TGG GCA TGA
Arg Leu Arg Glu Gly Asn Trp Ala  *
                165

GCC GTG GCA CTG GGG GCC CTG GTA ACT
Ala Val Ala Leu Gly Ala Leu Val Thr
            180                 185

AAG TG
Lys
```

*Fig. 9B (iii)*

| | |
|---|---|
| GTC CAG GAT TGG ATC GTG GCC<br>Val Gln Asp Trp Ile Val Ala<br>　　　　　　　125 | 384 |
| ATC CAC AGC AGT GGC GGC TGG<br>Ile His Ser Ser Gly Gly Trp<br>　　　　140 | 432 |
| GGG GCC CTG GAG GAC GCA CGG<br>Gly Ala Leu Glu Asp Ala Arg<br>　　　155　　　　　　　　160 | 480 |
| GTG AGC ACA GTG GTG ACG GGG<br>Val Ser Thr Val Val Thr Gly<br>170　　　　　　　175 | 528 |
| GTA GGG GCC TTT TTT GCT AGC<br>Val Gly Ala Phe Phe Ala Ser<br>　　　　　　　190 | 576 |
| | 582 |

Fig. 9B (iv)

MAMMALIAN GENE, BCL-W, BELONGS TO THE BCL-2 FAMILY OF APOPTOSIS-CONTROLLING GENES

The present invention is broadly directed to therapeutic molecules capable of inter alia modulating apoptosis in mammalian cells. The therapeutic molecules of the present invention encompass genetic sequences and chemical entities capable of regulating expression of a novel mammalian gene belonging to the bcl-2 family and which promotes cell survival. The therapeutic molecules of the present invention may have further utility in delaying cell cycle entry. In addition, the present invention extends to chemical entities capable of modulating activity and function of the translation product of said novel gene of the bcl-2 family. The present invention also extends to the translation product of the novel gene of the bcl-2 family and its use in, for example, therapy, diagnosis, antibody generation and as a screening tool for therapeutic molecules capable of modulating physiological cell death or survival and/or modulating cell cycle entry.

Bibliographic details of the publications numerically referred to in this specification are collected at the end of the description. Sequence Identity Numbers (SEQ ID NOs.) for the nucleotide and amino acid sequences referred to in the specification are defined following the Bibliography. A summary of the SEQ ID NOs. is provided before the Examples Throughout this specification, unless the context requires otherwise, the word "comprise", or variations such as "comprises" or "comprising", will be understood to imply the inclusion of a stated dement or integer or group of elements or integers but not the exclusion of any other element or integer or group of elements or integers.

The increasing sophistication of recombinant DNA technology is greatly facilitating research and development in the medical and allied health fields. This technology is becoming particularly important in research into the treatment and diagnosis of both proliferative cell disorders such as caners and sarcomas and in degenerative diseases such as some autoimmune conditions. There is a need to identify and characterise at the genetic level the elements involved in cell survival and physiological cell death (apoptosis).

Apoptosis is accomplished by a process that is conserved between organisms as diverse as nematodes and man. Positive and negative regulation of cell survival is essential for the proper development and differentiation of the embryo and for ensuring homeostasis in adult tissues. Cell survival can be promoted by the binding of growth factors to their receptors or by interaction of cellular adhesion molecules. A range of cytotoxic agents can counteract these signals and activate apoptosis, a process initially defined by specific morphologic criteria, such as chromatin condensation, cell compaction, membrane blebbing and, often, internucleosomal cleavage of DNA.

The biochemical details of the intracellular pathways governing cell survival and death remain largely undefined. However, several key regulators have emerged. The first to be discovered was Bcl-2, a 26 kD cytoplasmic protein encoded by the bcl-2 gene translocated to the IGH locus in human follicular lymphoma. High levels of Bcl-2 greatly enhance the ability of cells to survive cytokine deprivation and a wide variety of other cytotoxic conditions, including DNA damage.

The mammalian genome contains other genes homologous to bcl-2 but which differ in function. For example, bcl-x blocks apoptosis (Boise et al, 1993) whereas bar and bak inhibit the survival function of bcl-2 and bcl-x (Oltvai et al, 1993; Chittenden et al, 1995; Farrow et al., 1995; Kiefer et al, 1995). Due to the potential importance of cell apoptosis controlling genes in the treatment of cancers and sarcomas and in the treatment of degenerative disorders, there is a need to identify new genes homologous to bcl-2 in structure and function.

In accordance with the present invention, the inventors have identified a novel gene from mammals designated herein "bcl-w". Gene transfer studies show that bcl-w enhances cell survival and belongs to the bcl-2 family of apoptosis-controlling genes. The identification of this new gene will lead to the generation of a range of therapeutic molecules capable of acting as either antagonists or agonists of bcl-w expression or activity and will be useful in cancer or degenerative disease therapy. The identification of the gene will also permit the production of vast quantities of recombinant translation products for use in therapy, diagnosis, antibody generation and as a screen for therapeutic molecules capable of modulating physiological cell deaths or survival including modulating cell cycle entry.

Accordingly, the present invention is directed to a nucleic acid molecule comprising a nucleotide sequence encoding or complementary to a sequence encoding a novel mammalian gene from the bcl-2 family and comprising an amino acid sequence substantially as set forth in SEQ ID NO:7 or SEQ ID NO:9 or having 47% or greater similarity to either of SEQ ID NO:7 or SEQ ID NO:9.

Another aspect of the present invention is directed to a nucleic acid molecule comprising a nucleotide sequence encoding or complementary to a sequence encoding the amino acid sequence set forth in SEQ ID NO:7 or SEQ ID NO:9 or a derivative thereof or encoding an amino acid sequence having 47% or greater similarity to either SEQ ID NO:7 or SEQ ID NO:9.

The term "similarity" as used herein includes em identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level "similarity" includes amino acids that are nevertheless related to each other at the structural, functional, biochemical and/or conformational levels.

Preferably, the percentage similarity is between 48% and 100% inclusive such as approximately 50% or 55%, 59% or 65%, 70% or 75%, 80% or 85%, 90% or 95% or greater than 96% or a percentage similarity therebetween.

Another aspect of the present invention provides a nucleic acid molecule comprising a sequence of nucleotides substantially as set forth in SEQ ID NO:6 or SEQ ID NO:8 or a nucleotide sequence encoding an amino acid sequence having 47% or greater similarity to SEQ ID NO:7 or SEQ ID NO:9.

The nucleic acid molecule according to this aspect of the present invention corresponds herein to "bcl-w". This gene has been determined by the inventors in accordance with the present invention to enhance cell survival. The product of the bcl-w gene is referred to as Bcl-w. Human Bcl-w is defined by the amino acid sequence set forth in SEQ ID NO:7 and mouse Bcl-w is defined in SEQ ID NO:9. The respective nucleotide sequences from human bcl-w and mouse bcl-w are shown in SEQ ID NO:6 and SEQ ID NO:8 respectively. Reference herein to "bcl-w" includes reference to derivatives thereof includes single or multiple nucleotide substitutions, deletions and/or additions. Similarly, reference herein to "Bcl-w" includes all derivatives including amino acid substitutions, deletions and/or additions. The gene is preferably from a human, primate, livestock animal (sheep, pig, cow, horse, donkey), laboratory test animal (eg. mouse, at, rabbit, guinea pig), companion animal (eg. dog, cat) or captive wild animal (eg. fox, kangaroo, deer).

Although the present invention relates to a mammalian homologue of Bcl-w having an amino acid sequence of 47% or greater similarity to SEQ ID NO:7 or SEQ ID NO:8, the subject invention does extend to novel Bcl-w homologues from any animal including a mammal previously undisclosed.

Accordingly, another aspect of the present invention provides a nucleic acid molecule comprising a sequence of nucleotides encoding human Bcl-w or a derivative thereof, said human Bcl-w having an amino acid sequence substantially as set forth in SEQ ID NO:7 or is a mammalian homologue thereof having an amino acid sequence of substantially 47% or greater similarity to the amino acid sequence set forth in SEQ D NO:7.

A further aspect provides a nucleic acid molecule comprising a sequence of nucleotides encoding human Bcl-w or a derivative thereof, said murine Bcl-w having an amino acid sequence substantially as set forth in SEQ ID NO:9 or is a mammalian homologue thereof having an amino acid sequence of substantially 47% or greater similarity to the amino acid sequence set forth in SEQ ID NO:9.

The nucleic acid molecule of the present invention is preferably in isolated form or ligated to a vector, such as an expression vector. By "isolated" is meant a nucleic acid molecule having undergone at least one purification step and this is conveniently defined, for example, by a composition comprising at least about 10% subject nucleic acid molecule, preferably at least about 20%, more preferably at least about 30%, still more preferably at least about 40–50%, even still more preferably at least about 60–70%, yet even still more preferably 80–90% or greater of subject nucleic acid molecule relative to other components as determined by molecular weight, encoding activity, nucleotide sequence, base composition or other convenient means. The nucleic acid molecule of the present invention may also be considered, in a preferred embodiment, to be biologically pure.

The nucleic acid molecule encoding bcl-w is preferably a sequence of deoxyribonucleic acids such as cDNA sequence or a genomic sequence. A genomic sequence may also comprise exons and introns. A genomic sequence may also include a promoter region or other regulatory region. In a particularly preferred embodiment, the nucleotide sequence corresponding to bcl-w is a cDNA sequence comprising a sequence of nucleotides as set forth in SEQ ID NO:6 (human) or SEQ ID NO:8 (mouse) or is a derivative thereof including a nucleotide sequence having similar to SEQ ID NO:6 or SEQ ID NO:8 but which encodes an amino acid sequence having 47% or greater similarity to either SEQ ID NO:7 or SEQ ID NO:9.

The term "derivative" as used herein includes portions, fragments, parts, homologues or analogues of the nucleic acid molecule or a translation product thereof. A derivative may also be a single or multiple nucleotide or amino acid substitution, deletion and/or addition. A derivative of the nucleic acid molecule of the present invention also includes nucleic acid molecules capable of hybridizing to the nucleotide sequence set forth in SEQ ID NO:6 or SEQ ID NO:8 under low stringency conditions. Preferably, the low stringency is at 42° C.

More particularly, the present invention provides a nucleic acid molecule comprising a nucleotide sequence substantially as set forth in SEQ ID NO:6 or SEQ ID NO:8 or a derivative or homologue thereof capable of hybridizing to SEQ ID NO:6 or SEQ ID NO:8 under low stringency conditions and which encodes an amino acid sequence having 47% or greater similarity to the amino acid sequence set forth in SEQ ID NO:7 or SEQ ID NO:9.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

The derivatives of the nucleic acid molecule of the present invention include oligonucleotides, PCR primers, antisense molecules, molecules suitable for use in co-suppression and fusion nucleic acid molecules. Some molecules are also contemplated capable of regulating expression of bcl-w. The present invention also contemplates ribozymes directed to bcl-w. The derivatives of the Bcl-w translation product of the present invention include fragments having particular epitopes or parts of the entire Bcl-w protein fused to peptides, polypeptides or other proteins. Catalytic antibodies are also contemplated to Bcl-w or derivatives thereof. Such catalytic antibodies would be useful for controlling or otherwise modulating Bcl-w. The catalytic antibodies or other regulatory molecules may need to be modified to facilitate entry into the cells. Alternatively, they may be genetically produce in transgenic cells or introduced via a viral or other suitable vector.

In another embodiment the present invention is directed to an isolated nucleic acid molecule encoding bcl-w or a derivative thereof, said nucleic acid molecule selected from the list consisting of:

(I) a nucleic acid molecule comprising a nucleotide sequence encoding the amino acid sequence set forth in SEQ ID NO:7 or SEQ ID NO:9 or having 47% or greater similarity for SEQ ID NO:7 or SEQ ID NO:9;

(ii) a nucleic acid molecule comprising a nucleotide sequence substantially as set forth in SEQ ID NO:6 or SEQ ID NO:8 or comprising a nucleotide sequence encoding an amino acid sequence of 47% or greater similarity to SEQ ID NO:7 or SEQ ID NO:9;

(iii) a nucleic acid molecule capable of hybridizing to the nucleotide sequence substantially set forth in SEQ ID NO:6 or SEQ ID NO:8 under low stringency conditions and encoding an amino acid sequence having of 47% or greater similarity to SEQ ID NO:7 or SEQ ID NO:9;

(iv) a nucleic acid molecule capable of hybridizing to the nucleic acid of part (I) or (ii) or (iii) under low stringency conditions and encoding an amino acid sequence having 47% or greater similarity to SEQ ID NO:7 or SEQ ID NO:9; and (v) a derivative or mammalian homologue of the nucleic acid molecule of parts (I) or (ii) or (iii) or (iv).

The mammalian homologues contemplated in part (v) of the previous paragraph are novel homologues and do not encompass, for example, known Bcl-2. As stated above, novel homologues of Bcl-w falling outside of the definition herein described are also contemplated y the present invention.

The nucleic acid molecule may be ligated to an expression vector capable of expression in a prokaryotic cell (e.g. E.coli) or a eukaryotic cell (e.g. yeast cells, fungal cells, insect cells, mammalian cells or plant cells). The nucleic acid molecule may be ligated or fused or otherwise associated with a nucleic acid molecule encoding another entity such as a signal peptide, a cytokine or other member of the Bcl-2 family.

The present invention extends to the expression product of the nucleic acid molecule hereinbefore defined.

The expression product is Bcl-w having an amino acid sequence set forth in SEQ ID NO:7 or SEQ ID NO:9 or is a derivative thereof as defined above or is a mammalian homologue having an amino acid sequence of 47% or greater similarity to the amino acid sequence set forth in SEQ ID NO:7 or SEQ ID NO:9. A derivative may be a single or multiple amino acid substitution, deletion and/or addition. Other derivatives include chemical analogues of Bcl-w. Analogues of Bcl-w contemplated herein include, but are not limited to, modification to side chains, incorporating of unnatural amino acids and/or their derivatives during peptide, polypeptide or protein synthesis and the use of crosslinkers and other methods which impose confirmational constraints on the proteinaceous molecule or their analogues.

Another aspect of the present invention is directed to an isolated polypeptide selected from the listing consisting of:
(I) a polypeptide having an amino acid sequence substantially as set forth in SEQ ID NO:7 or SEQ ID NO:9 or a sequence having 47% or greater similarity to SEQ ID NO:7 or SEQ ID NO:9;
(ii) a polypeptide encoded by a nucleotide sequence substantially as set forth in SEQ ID NO:6 or SEQ ID NO:8 or a sequence encoding an amino acid sequence having 47% or greater similarity to SEQ ID NO:7 or SEQ ID NO:9;
(iii) a polypeptide encoded by a nucleic acid molecule capable of hybridizing to the nucleotide sequence set forth in SEQ ID NO:6 or SEQ ID NO:8 under low stringency conditions and which encodes an amino acid sequence substantially as set forth in SEQ ID NO:7 or SEQ ID NO:9 or an amino acid sequence having 47% or greater similarity to SEQ ID NO:7 or SEQ ID NO:9;
(iv) a polypeptide as defined in part (I) or (ii) or (iii) in homodimeric form; and
(v) a polypeptide as defied in part (I) or (ii) or (iii) in heterodimeric form.

A derivative may carry a mutation anywhere in the Bcl-w molecule such as but not limited to the S1 and/or S2 region. For example, a substitution at position 94 in S2 from Gly to Glu is encompassed by the present invention. Other areas of Bcl-w for which mutations are contemplated include but are not limited to the region immediately N-terminal to S2, the NH1 region, the S3 region, the S2–S3 region and the BH3 region.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 1.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The identification of bcl-w permits the generation of a range of therapeutic molecules capable of modulating expression of bcl-w or modulating the activity of Bcl-2. Modulators contemplated by the present invention includes agonists and antagonists of bcl-w expression. Antagonists of bcl-w expression include antisense molecules, ribozymes and co-suppression molecules. Agonists include molecules which increase promoter ability or interfere with negative regulatory mechanisms. Agonists of Bcl-w include molecules which overcome any negative regulatory mechanism. Antagonists of Bcl-w include antibodies and inhibitor peptide fragments.

TABLE 1

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginie | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |

TABLE 1-continued

| Non-conventional amino acid | Code |
|---|---|
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcystcine | Nmcys |
| L-N-methylglutamine | Nmgln |
| L-N-methylglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cyclododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |

TABLE 1-continued

| Non-conventional amino acid | Code |
| --- | --- |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-3,3-diphenylpropyl) carbamylmethyl)glycine | Nnbhe |

The Bcl-w of the present form may be in multimeric form meaning that two or more molecules are associated together. Where the same Bcl-w molecules are associated together, the complex is a homomultimer. An example of a homomultimer is a homodimer. Where at least one Bcl-w is associated with at least one non-Bcl-w molecule, then the complex is a heteromultimer such as a heterodimer. A heteromultimer may include a molecule another member of the Bcl-2 family or a molecule capable of promoting cell survival.

The present invention contemplates, therefore, a method for modulating expression of bcl-w in a mammal said method comprising contacting the bcl-w gene with an effective amount of a modulator of bcl-w expression for a time and under conditions sufficient to up-regulate or down-regulate or otherwise modulate expression of bcl-w. For example, a nucleic acid molecule encoding Bcl-w or a derivative thereof may be introduced into a cell to enhance the ability of that cell to survive, conversely, bcl-w antisense sequences such as oligonucleotides may be introduced to decrease the survival capacity of any cell expressing the endogenous bcl-w gene.

Another aspect of the present invention contemplates a method of modulating activity of Bcl-w in a mammal, said method comprising admit g to said mammal a modulating effective amount of a molecule for a time and under conditions sufficient to increase or decrease Bcl-w activity. The molecule may be a proteinaceous molecule or a chemical entity and may also be a derivative of Bcl-w or its receptor.

Increased bcl-w expression or Bcl-w activity may be influential in regulating inhibition or prevention of cell degeneracy such as under cytotoxic conditions during, for example, γ-irradiation and chemotherapy. Decreased bcl-w expression or Bcl-w activity may be important, for example, in selective cancer therapy and increased bcl-w expression may be important for treatment or prophylaxis of conditions such as stroke and Alzheimer's disease.

Accordingly, the present invention contemplates a pharmaceutical composition comprising a modulator of bcl-w expression or Bcl-w activity and one or more pharmaceutically acceptable carriers and/or diluents.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved at the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a stile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When bcl-w and Bcl-w modulators are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 ug and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of modulating bcl-w expression or Bcl-w activity. The vector may, for example, be a viral vector.

Conditions requiring modulation of physiological cell death include enhancing survival of cells in patients with neurodegenerative diseases, myocardial infarction, muscular degenerative disease, hypoxia, ischaemia, HIV infection or for prolonging the survival of cells being transplanted for treatment of disease. Alternatively, the antisense sequence could be used, for example, to reduce the survival capacity of tumour cells or autoreactive lymphocytes. The sense sequence may also be used for modifying in vitro behaviour of cells, for example, as part of a protocol to develop novel lines from cell types having unidentified growth factor requirements; for facilitating isolation of hybridoma cells producing monoclonal antibodies, as described below; and for enhancing survival of cells from primary explants while they are being genetically modified.

Still another aspect of the present invention is directed to antibodies to Bcl-w and its derivatives including catalytic antibodies. Such antibodies may be monoclonal or polyclonal and may be selected from naturally occurring antibodies to Bcl-w or may be specifically raised to Bcl-w or derivatives thereof. In the case of the latter, Bcl-w or its derivatives may first need to be associated with a carrier molecule. The antibodies and/or recombinant Bcl-w or its derivatives of the present invention are particularly useful as therapeutic or diagnostic agents. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regima.

For example, Bcl-w and its derivatives can be used to screen for naturally occurring antibodies to Bcl-w. These may occur, for example in some autoimmune diseases.

For example, specific antibodies can be used to screen for Bcl-w proteins. The latter would be important, for example, as a means for screening for levels of Bcl-w in a cell extract or other biological fluid or purifying Bcl-w made by recombinant means from culture supernatant fluid. Techniques for the assays contemplated herein are known in the art and include, for example, sandwich assays, ELISA and flow cytometry.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of Bcl-w.

Both polyclonal and monoclonal antibodies are obtainable by immunization with the protein or peptide derivatives and either type is utilizable for immunoassays. The methods of obtaining both types of sera are well known in the art. Polyclonal sera are less preferred but are relatively easily prepared by injection of a suitable laboratory animal with an effective amount of Bcl-w, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology* Vol II, ed. by Schwartz, 1981; Kohler and Milstein, *Nature* 256: 495–499, 1975; *European Journal of Immunology* 6: 511–519, 1976).

Another aspect of the present invention contemplates a method for detecting Bcl-w in a biological sample from a subject said method comprising contacting said biological sample with an antibody specific for Bcl-w or its derivatives or homologues for a time and under conditions sufficient for an antibody-Bcl-w complex to form, and then detecting said complex.

The presence of Bcl-w may be accomplished in a number of ways such as by Western blotting, ELISA or flow cytometry procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain Bcl-w including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the Bcl-w or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducing an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minute) and under suitable conditions (e.g. 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect bcl-w or its derivatives.

The present invention is further described by reference to the following non-limiting figures and examples.

In the Figures:

FIG. 1 is a representation showing predicted amino acid sequences encoded by murine bcl-w cDNAs (top line, "Bcl-w", SEQ ID NO: 9) and chimaeric cDNAs corresponding to transcripts spliced from exon 3 of the bcl-w gene to an exon of the adjacent rox gene (bottom line, "Bcl-w-Rox", SEQ ID NO: 10). Boxes highlight the regions of highest homology within the Bcl-2 family, denoted S1, S2 and S3 (Cory, 1995). The arrowhead marks the position corresponding to an intron within the gene. Two residues that differ in human Bcl-w are indicated above the mouse sequence. Not all of the rox cDNA sequences was determined in both orientations.

Figure 2:
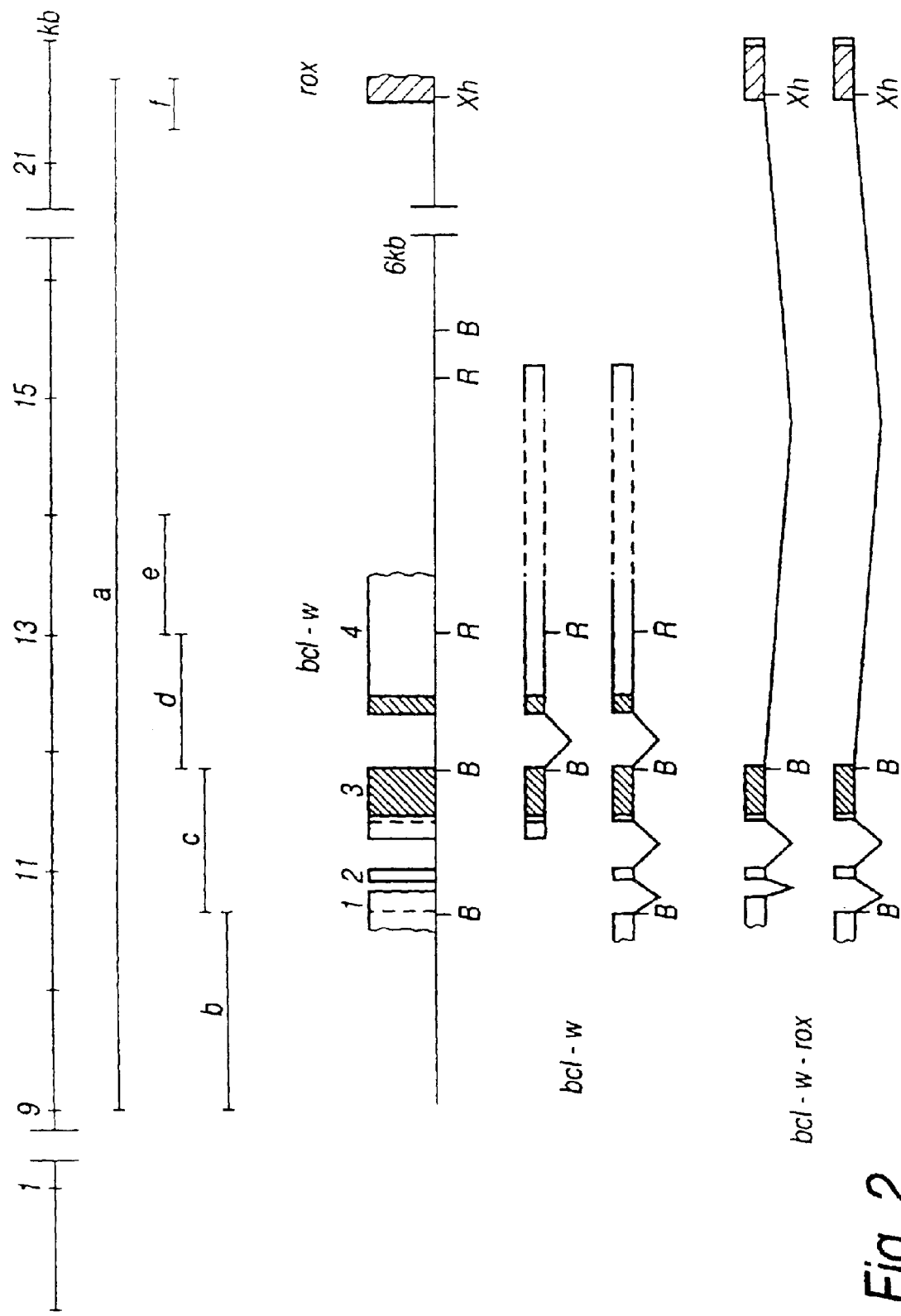

FIG. 2 is a diagrammatic representation showing the structure of the genomic bcl-w locus and derivation of the bcl-w and bcl-w/rox cDNAs. Overlapping genomic fragments encompassing a 22 kb region were cloned, only one of which (a) is shown. Fragments b to f are subclones of fragment a. Exons are denoted as boxes, with non-coding regions open, the coding region of the bcl-w gene filled and that of the rox gene (see text) stippled. Two types of 5'-end were found for each class of mRNA, suggestive of alternative promoters and/or splicing The first 815 residues of the 3' untranslated region of bcl-w correspond precisely to those in genomic exon 4; the region not yet sequenced is indicated as a broken line. Restriction mapping suggests the 3' untranslated region of bcl-w contains at least one more intron. The location of the remainder of the rox gene is not known.

Figure 3:
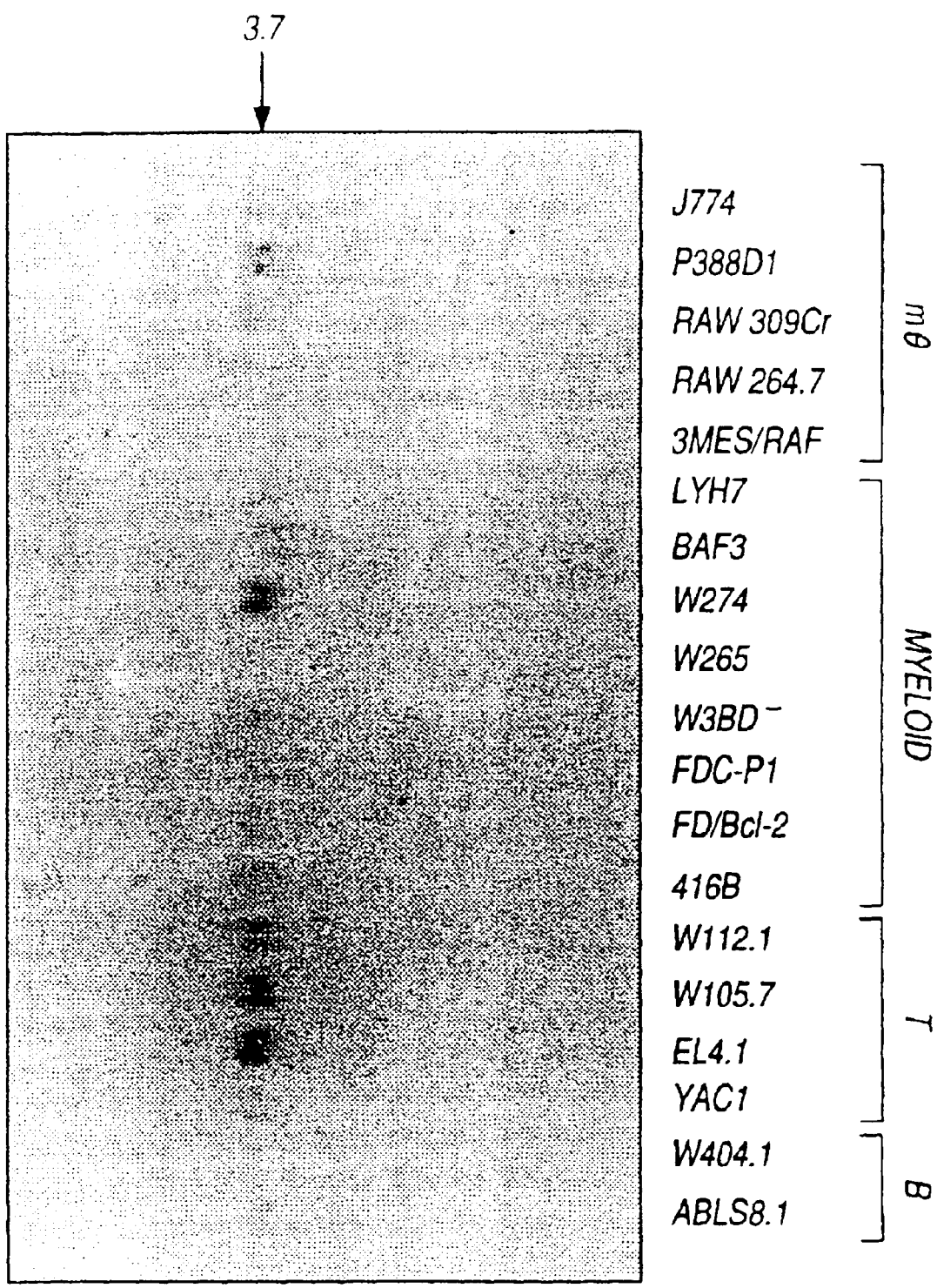

FIG. 3 is a photographic representation showing expression of bcl-w RNA in haemopoietic cell lines. Polyadenylated RNA prepared from the indicated macrophage (mϕ), myeloid, and T and B lymphoid lines was fractionated by electrophoresis, transferred to nitrocellulose filters and hybridised with a bcl-w cDNA probe. Probes from the coding region and the bcl-w 3' untranslated region gave identical results.

Figure 4A:
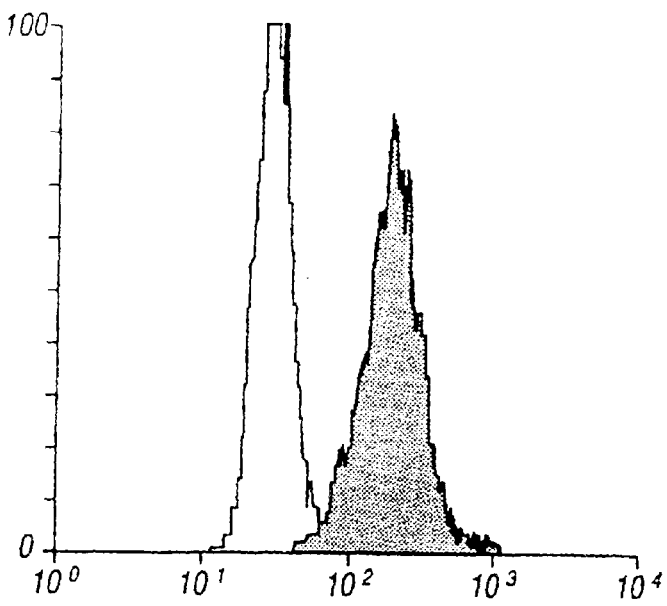
Figure 4B:
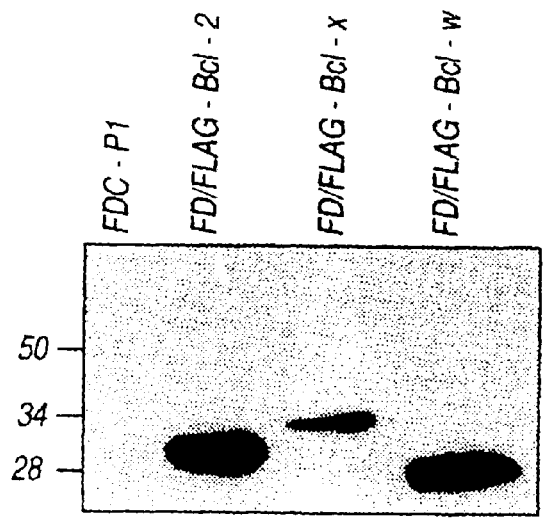

FIG. 4 shows the expression of Bcl-w protein. (A) Expression of FLAG-Bcl-w within a clone (D3B5) of FDC-P1 cells transfected with the FLAG-bcl-w PGKpuro expression vector. Transfectants (filled) and parental cells (open) were stained with anti-FLAG monoclonal antibody and analysed by flow cytometry. (B) Immunoblots revealing epitope-tagged survival proteins. Lysates of FDC-P1 cells and FDC-P1 cells expressing FLAG-tagged mouse Bcl-w (clone D3B5), human Bcl-$x_L$ or human Bcl-2 were passed over an anti-FLAG affinity gel (Kodak), eluted with FLAG peptide, fractionated by electrophoresis and then analysed with anti-FLAG antibody. (C) Immunoblots with polyclonal rabbit anti-Bcl-w antiserum on cell lysates fractionated by SDS-polyacrylamide gel electrophoresis. In (B) and (C), the stained proteins were visualise by enhanced chemiluminescence (Amersham). WEHI-112.1 and EL4.1 are T lymphoma lines (Harris et al., 1973) and J774 is a macrophage line (Ralph et al., 1975). An additional protein of ~18 kD was also detected by the antiserum, apparently by fortuitous cross-reaction. The molecular weights of markers (Bio-Rad) are given in kD.

FIG. 5 is a graphical representation showing that Bcl-w inhibits apoptosis induced by several but not all cytotoxic agents. FDC-P1 cells, which require IL-3 for survival and proliferation (Dexter et al., 1980), were either (A, left panel) washed three times in medium lacking IL-3 or (A, right panel) irradiated (10 Gy) and then cultured in medium lacking (A, left panel) or containing IL-3 (A, right panel). B6.2.16BW2 T hybridoma cells (Teh et al., 1989) were either cultured in medium containing 1 μM dexamethasone (B, left panel) or irradiated (10 Gy) (B, right panel). CH1 B lymphoma cells (Lynes et al., 1978) were either cultured in the presence of 0.1 μg/ml Jo2 anti-mouse CD95 antibody (Ogasawara et al., 1993) (C, left panel) or irradiated (10 Gy) (C, right panel). Cultures were initiated at $2.5 \times 10^5$ cells/ml and viability determined by staining with 0.4% w/v eosin on the indicated days.

Figure 6:
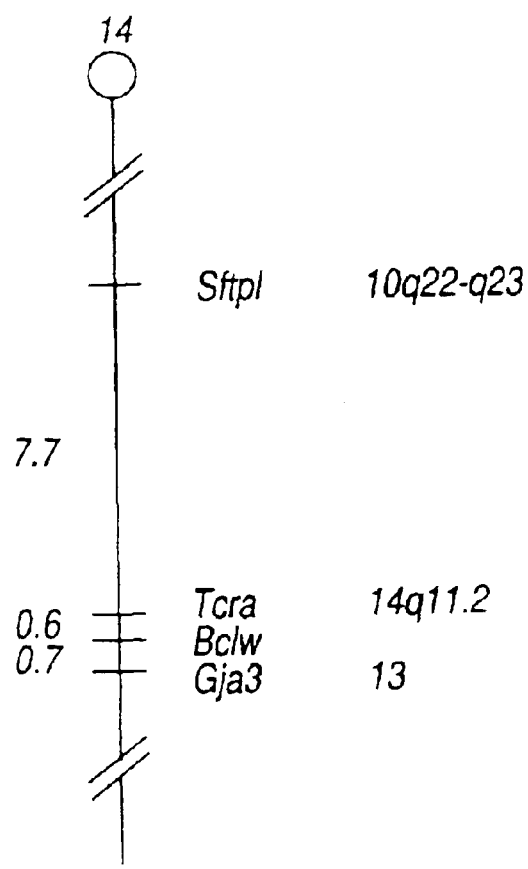

FIG. 6 is a diagrammatic representation showing that Bcl-w maps in the central region of mouse chromosome 14. The segregation patterns of bcl-w and flanking genes in 134 backcross animals typed for all loci are shown at the top. Each column represents the haplotype inherited from the (C57BL/6J×M. spretus) $F_1$ parent; shaded boxes represent the C57BL/6J allele and open boxes the M. spretus allele. The number of offspring inheriting each type of chromosome is listed below each column. A partial chromosome 14 linkage map showing the location of bcl-w in relation to linked genes is shown at the bottom. Recombination distances between loci in centiMorgans are shown to the left of the chromosome and the positions of loci in human chromosomes, where known, are shown to the right References for the human map positions of loci cited in this study can be obtained from GDB (Genome Data Base), a database of human linkage information maintained by The William H. Welch Medical Library of The Johns Hopkins University (Baltimore, Md.).

Figure 7A:
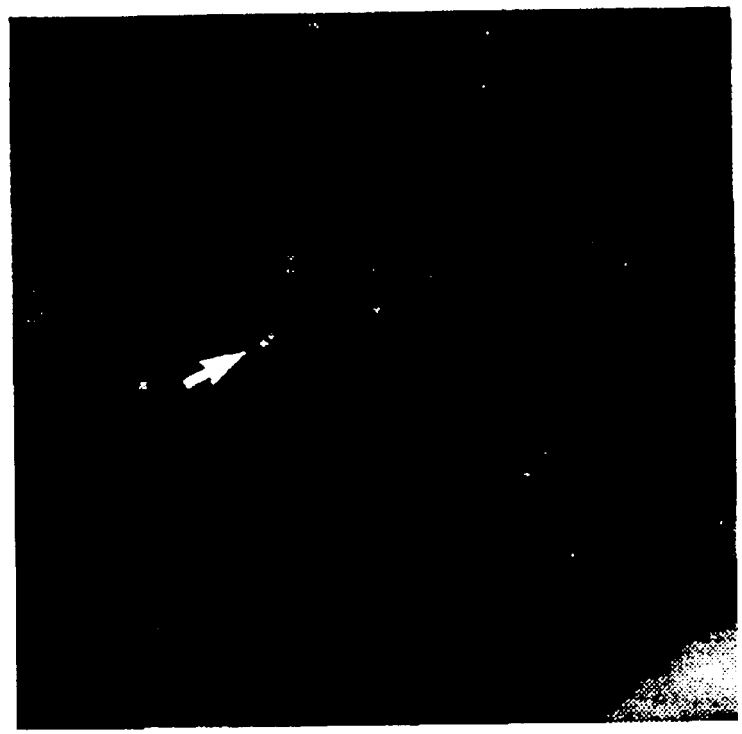
Figure 7B:

FIG. 7 is a photographic representation showing localisation of bcl-w on human chromosome 14. Partial metaphase showing FISH with the bcl-w intronic probe. (A) Normal male chromosomes stained with propidium iodide. Hybridisation sites on chromosome 14 are indicated by an arrow. (B) the same metaphase as in (A) stained with DAPI for chromosome identification.

FIG. 8 is a representation of a comparison of survival and anti-survival Bcl-2 sub-families. Human Bcl-2 (SEQ ID NO: 11), Bcl-$x_L$ (SEQ ID NO: 12), Bcl-w (SEQ ID NO: 7), Bax (SEQ ID NO: 13) and Bak (SEQ ID NO: 14) amino acid sequences were aligned by the Wisconsin PILEUP program. The most conserved portion of the Ced 9 sequence (SEQ ID NO: 15) and a short conserved segment in Bik are also shown. Gaps made in individual sequences to optimise alignment are indicated by dots. Residues identical or very similar (L~M; E~D; K~R; V~I) in the survival-promoting proteins Bcl-2, Bcl-$x_L$ and Bcl-w are shown on a black background, as are also those identical or very similar in all the Bcl-2 homologues. A grey background indicates residues shared by Bak and Bax but not present in the survival proteins. Homology regions S1, S2 and S3 (Cory, 1995) and the hydrophobic C-terminal segment are boxed, while the BH1, BH2, BH3 and NH1 regions defined by others (Yin et al., 1994; Subramanian et al., 1995) are overlined. Filled arrowheads indicate conserved residues specific to the survival proteins; open arrowheads, those specific to anti-survival proteins. An unbroken arrow indicates the position of the splice site common to all the proteins; a broken arrow, the position of the alternative 5' splice that creates the smaller Bcl-x protein and a wavy line a conserved C-terminal motif.

FIG. 9 is a representation of the coding region of (A) human (SEQ ID NO: 6) and (B) murine (SEQ ID NO: 8) bcl-w.

Single and triple letter abbreviations for amino acid residues are used in the subject specification, as defined in Table 2.

TABLE 2

AMINO ACID ABBREVIATIONS

| Amino Acid | Three-letter Abbreviation | One-letter Symbol |
|---|---|---|
| Alanine | Ala | A |
| Arginine | Arg | R |

TABLE 2-continued

AMINO ACID ABBREVIATIONS

| Amino Acid | Three-letter Abbreviation | One-letter Symbol |
|---|---|---|
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

SUMMARY OF SEQ ID NOs.

| SEQ ID NO. | DESCRIPTION |
|---|---|
| 1 | 5' Primer for Mouse bcl-w (together with an XbaI site) |
| 2 | Amino acid sequence for SEQ ID NO:1 |
| 3 | 3' Primer for Mouse bcl-w (together with an EcoR1 site) |
| 4 | Amino acid sequence for SEQ ID NO:3 |
| 5 | N-terminal amino acid sequence of Mouse Bcl-w |
| 6 | Human bcl-w |
| 7 | Human Bcl-w |
| 8 | Mouse bcl-w |
| 9 | Mouse Bcl-w |

EXAMPLE 1

PCR Cloning

Based on the strong homology between Bcl-2, Bcl-$x_L$ and Bax, degenerate PCR primers were designed within the S2 and S3 regions (see FIG. 8), using inosine at totally degenerate positions. To facilitate cloning, Xba I and Eco RI restriction sites were incorporated at the ends. The 5' primer was 5'GCTCTAG AAC TGG GGI (AC)GI (AG)TI GTI GCC TT(CT) TT3' [SEQ ID NO:1], corresponding to Xba I—NWGR(IV)VAFF [SEQ ID NO:2], and the 3' primer was 5'GGAAT TC CCA GCC ICC IT(GT) ITC TTG GAT CCA 3' [SEQ ID NO:3], corresponding to WIQ(DE)(NQ)GGW—Eco RI [SEQ ID NO:4]. Polyadenylated RNA templates (1 μg) for reverse transcription came from the mouse macrophage cell line J774 and d18 mouse brain. The RNA was ethanol precipitated, dried, resuspended in 10 μl of water, heated at 65° C. for 10 min and chilled on ice. It was then reverse transcribed in a 20 μl reaction containing 50 mM TrisHCl (pH8.3 at 25° C.), 75 mM KCl, 3 mM MgCl$_2$, 10 mM dithiothreitol 0.5 mM dNTPs, 2 μl random hexamer primers (Amersham First Strand cDNA Synthesis System) and 200 U Superscript II™ reverse transcriptase (GIBCO), at 48° C. for 60 min. For the PCR reaction, 1 μl of this reaction mixture was added to 49 μl of a cocktail consisting of 50 mM KCl, 10 mM TrisHCl (pH 9.0 at 25° C.), 0.1% v/v Triton X-100, 1.5 mM MgCl$_2$, 0.2 mM dNTPs, 10% v/v glycerol, 0.05% w/v gelatine, 0.3 μg of each primer and 2.5 U Taq DNA polymerase. This mixture was denatured at 94° C. for 3 min, then subjected to 5 cycles comprising 1 min at 94° C., 2 min at 37° C., ramping at 0.3° C./sec to 72° C. followed by 1 min at 72° C. The thermal profile for the following 35 cycles was 1 min at 94° C., 2 min at 42° C., 1 min at 72° C. Finally, the mixture was incubated at 72° C. for 5 min. The PCR products were fractionated by gel electrophoresis and DNA fragments of the expected size (159 bp) were extracted from the gel, restricted with Eco RI and Xba I and subcloned into Eco RI/Xba I-digested pBluescript II SK(+). The resulting clones were sequenced using a single base (T) reaction using the fmol™ Sequencing System (Promega) and the manufacturer's protocol. Complete sequence analysis was then performed on a representative clone for each unique T-track pattern.

EXAMPLE 2

Interspecific Mouse Backcross Mapping

Interspecific backcross progeny were generated by mating (C57BL/6J×M. spretus)F$_1$ females and C57BL/6J males as described (Copeland and Jenkins, 1991). A total of 205 N$_2$ mice were used to map the Bcl-w locus. DNA isolation, restriction enzyme digestion, agarose gel electrophoresis, Southern blot transfer and hybridisation were performed essentially as described (Jenkins et al., 1982). The probe, a 2.6 kb EcoRI/NolI fragment of mouse cDNA, was labelled with ($\alpha^-$P) dCTP using a random primed labelling kit (Stratagene); washing was done to a final stringency of 1.0×SSCP, 0.1% w/v SDS, 65° C. A fragment of 3.8 kb was detected in BamHI digests of C57BL/6J DNA and 7.8 kb in M. spretus DNA. Their distribution was followed in backcross mice. The probes and RFLPs for the loci linked to bcl-w, including surfactant associated protein 1 (Sftp1), T cell receptor alpha chain (Tcrα), and gap junction membrane channel protein alpha-3 (Gjα3), have been described previously (Haefliger et al., 1992; Moore et al., 1992). Recombination distances were calculated as described (Green, 1981) using the computer program SPRETUS MADNESS. Gene order was determined by minimising the number of recombination events required to explain the allele distribution patterns.

EXAMPLE 3

Fluorescence IN SITU Hybridisation (Fish)

cDNA and intron probes were nick-translated with biotin-14-dATP and hybridised in situ at a final concentration of 20 ng/ml to normal male metaphases. The FISH method was modified from that previously described (Callen et al., 1990) in that chromosomes were stained before analysis with both propidium iodide (as counterstain) and 4,6-diamidino-2-phenylindole (DAPI) (for chromosome identification). Images of metaphase preparations were captured by a CCD camera and computer enhanced.

EXAMPLE 4

Expression Vectors

The plasmid vector used for expression and selection in eukaryotic cells is based on the pEFBos vector containing the potent promoter (and splice) from the highly expressed elongation factor la gene and contains a selectable marker (puroR) driven by the PGK promoter (Mizushima and Nagata, 1990; Visvader et al., 1992). A FLAG epitope tag (Hopp et al., 1988) was incorporated to aid identification of the protein product. The bcl-w cDNA was inserted into pEF FLAG-X-PGKpuro, sequenced to confirm the reading frame and transfected by electroporation into FDC-P1 (Dexter et al., 1980), B6.2.16BW2 (The et al., 1989) and CH1 (Lynes et al., 1978) cells. Transfectants were selected by culture for 7 days in medium containing 2 µg/ml puromycin and clones subsequently derived from independent pools by limiting dilution.

To detect FLAG-tagged proteins by cytoplasmic immunofluorescence, cells were fixed for a 5 min in 80% v/v methanol at −20° C. and then permeabilised with 0.3% saponin (Sigma), which was included in all subsequent staining and washing steps. The cells were first incubated with the primary M2 monoclonal antibody (Eastman-Kodak, New Haven, Conn.) for 40 min on ice, then decorated with fluoroscein-isothiocyanate (FITC)-conjugated goat anti-mouse IgG (1–2 µg/ml; Southern Biotechnology, Birmingham) and analysed by flow cytometry using the FACScan (Becton Dickinson).

EXAMPLE 5

Bcl-w Antibody

Rabbit polyclonal anti-Bcl-w antibodies were raised against the N-terminal peptide Ac-MATPASTPDRALV-NH2 [SEQ ID NO:5] (Chiron Mimotopes). KLH-conjugated peptide (100 µg in 0.5 ml of phosphate-buffered saline with an equal volume of Freund's adjuvant) was injected into rabbits and 3, 7 and 14 weeks later the animals were boosted with the same peptide but in Freund's incomplete adjuvant. The rabbit antisera were screened by ELISA against the BSA-conjugated peptide.

EXAMPLE 6

Identification of a Novel bcl-2-Related Gene

Degenerate PCR primers encoding part of the S2 and S3 regions of the three bcl-2 homologues known at the time (bcl-2, bcl-x and bax) were used for low-stringency amplification of cDNA templates derived from mRNA of a mouse macrophage cell line and mouse brain (see Example 1). Fragments of the size (159 bp) expected for known Bcl-2 family members were subcloned and screened by sequencing. As anticipated, multiple bcl-2, bcl-x and bax clones were identified, but both RNA sources also yielded clones representing a novel gene. To obtain a full length cDNA, the cloned PCR product was used to probe cDNA libraries from adult mouse brain, spleen and a myeloid cell line. Two classes of cDNA were obtained (FIG. 1). The first encoded a polypeptide strikingly similar to Bcl-2, which we termed Bcl-w. The second encoded a much larger polypeptide, which was identical to Bcl-w for the first 144 residues but then diverged markedly. The point of divergence was within the S3 region at a point corresponding to a splice unction in the bcl-2, bcl-x and bax genes. It thus seemed likely that the second class of RNA was produced by alternative splicing of bcl-w transcripts.

To resolve this issue, overlapping genomic clones encompassing 22 kb of the bcl-w locus (FIG. 2) were isolated. The N-terminal portion of the coding region mapped to a 1.3 kb BamHI fragment (subclone c). Its sequence and that of adjacent fragments were determined. Comparison with sequences of the first class of cDNAs revealed that the bcl-w gene contained at least 4 closely spaced exons with the coding region split between exon 3 and 4. The unusually large (~2.8 kb) 3' untranslated region begins in exon 4. Probes corresponding to either the coding region or the 3' untranslated region of these bcl-w cDNAs hybridised to a 3.7 kb polyadenylated RNA of relatively low abundance (FIG. 3). The largest bcl-w cDNAs are nearly that long.

The second class of cDNAs proved to correspond to chimaeric RNAs produced from bcl-w and an adjacent gene (FIG. 2). The genomic and cDNA sequences diverge at the 3' end of exon 3, and the 3' portion of the cDNAs derives from an exon approx 9.2 kb downstream (FIG. 2).

A database search revealed strong homology between the downstream exon and rox2 gene of Drosophila The predicted mouse rox-amino acid sequence of 66% identity and 79% similarity with Drosophila gene, which may encode an RNA binding protein (Brand et al, 1995). Thus, alternative splicing generates blc-w/rox transcripts. The location of the remainder of the murine rox gene awaits isolation of further genomic clones.

A probe specific for rox of Drosophila (see Brand et al, 1995) hybridised to abundant mRNAs of 2.8 and 1.8 kb, presumably the bonafide (non-chimaeric) transcripts of the rox gene. Since cDNA probes corresponding to exon 3 of bcl-w detected only the 3.7 kb RNA, the chimaeric bcl-w/rox transcripts appear to be of low abundance. The significance of the bcl-w/rox transcripts is unclear, and our inability to express detectable levels of the corresponding protein has thus far precluded further analysis.

EXAMPLE 7

THE Human and Mouse bcl-w Genes are Highly Homologous

Human bcl-w cDNAs were isolated from a library derived from adult brain mRNA. All six clones corresponded to bcl-w cDNA and no chimaeric cDNAs were detected. The coding regions of the human and mouse genes were extremely homologous: 99% identical at the amino acid level and 94% at the nucleotide level. The only amino acid differences were two conservative substitutions: alanine instead of threonine at residue 7 and glutamic acid rather than aspartic acid at residue 124, just upstream of the S3 region. By comparison, the homology of the human and mouse bcl-2 coding regions is 90% at the amino acid level and 88% at the nucleotide level, and that of bcl-x is 97% and 94%.

EXAMPLE 8

The bcl-w Gene Enhances Cell Survival

Figure 4C:
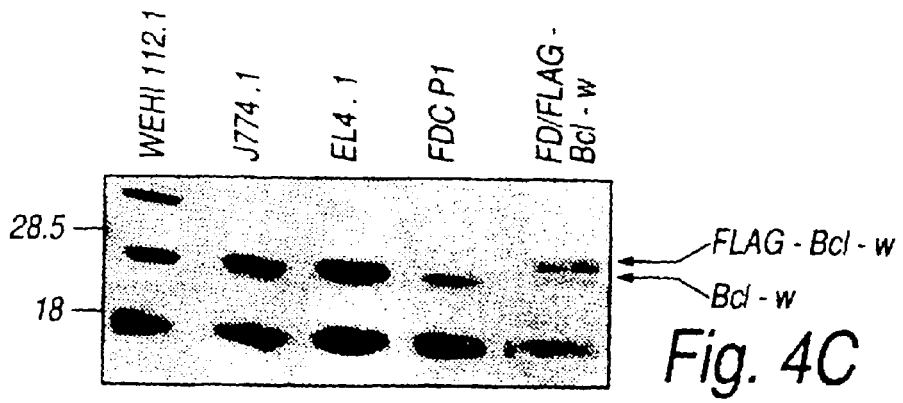

To allow tests on its function, the bcl-w cDNA was inserted into expression vectors and transfected into three haemopoietic cell lines: FDC-P1, an IL-3 dependent myeloid line; B6.2.16BW2, a T hybridoma line; and CH1, a B lymphoma line. To facilitate detection, the recombinant protein included an N-terminal FLAG epitope (Hopp et al., 1988). Several independent pools and clones of drug-resistant cells that stained strongly with an anti-FLAG monoclonal antibody (e.g. FIG. 4A) were selected for study. Western blot analysis FIG. 4B) showed that the FLAG-Bcl-w protein had an apparent molecular weight of 25 kD. Rabbit antiserum raised to an N-terminal peptide of Bcl-w detected not only the FLAG-tagged protein but also a protein of ~22 kD, presumably endogenous Bcl-w, that was also apparent in lysates of four untransfected cell lines (FIG. 4C). The mobility of the endogenous protein was indistinguishable from that of Bcl-w lacking the FLAG tag transiently expressed in COS cells.

Bcl-w has a hydrophobic region close to its carboxy-terminus and would therefore be expected to be membrane-associated. Confocal microscopy of FDC-P1 cells transfected with a bcl-w expression vector and stained with the rabbit polyclonal antibody demonstrated that Bcl-w was located in the cytoplasm and that its distribution closely resembled that of Bcl-2. The cytoplasmic localisation of Bcl-w was confirmed by western blots of nuclear and cytoplasmic protein fractions.

Figure 5A:
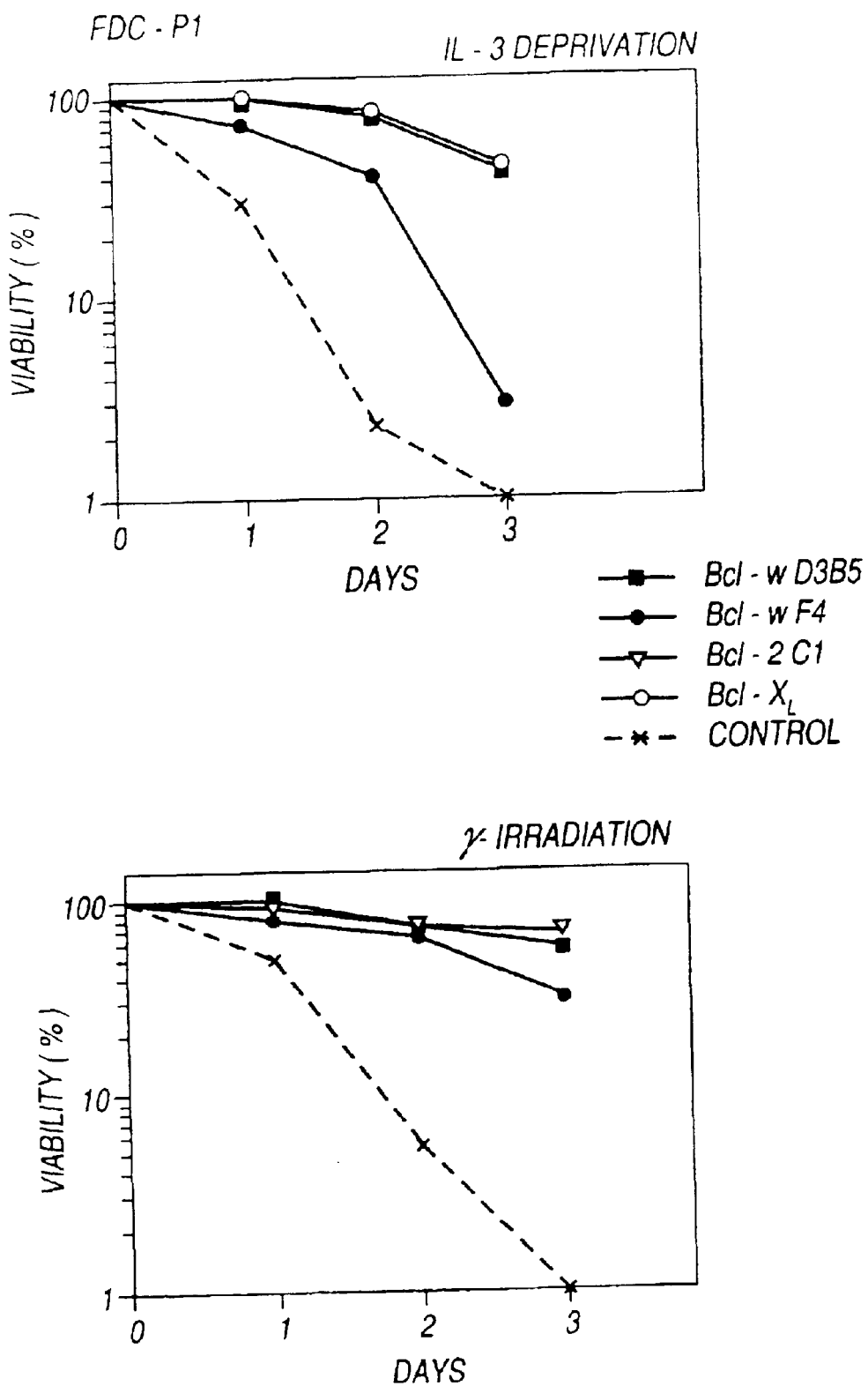
Figure 5B:
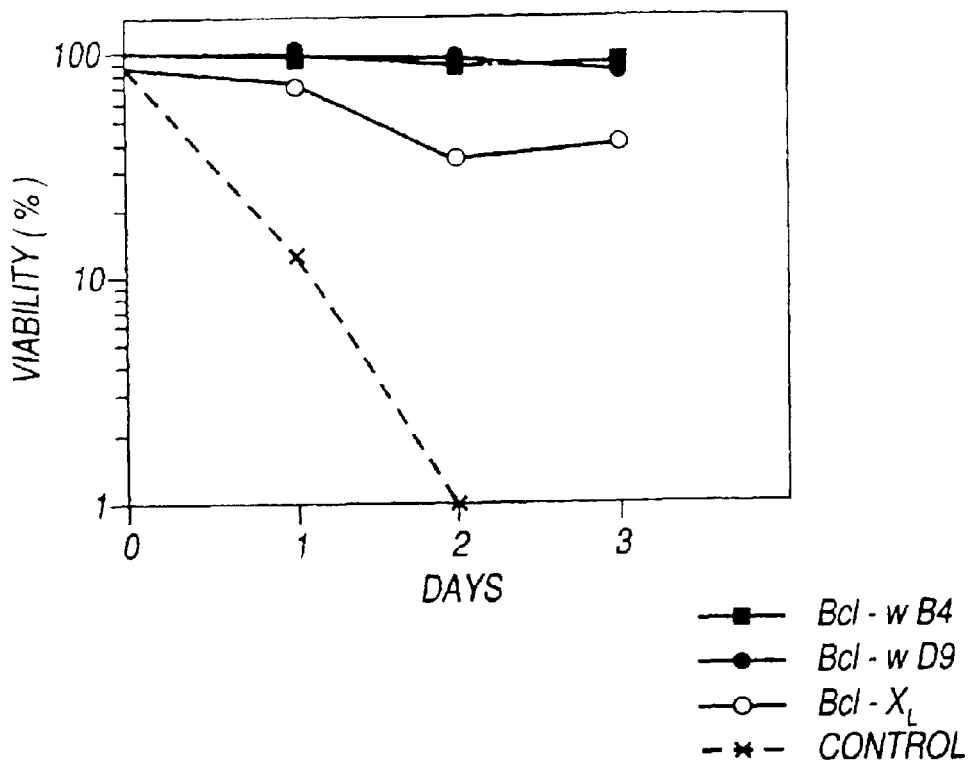
Figure 5B:
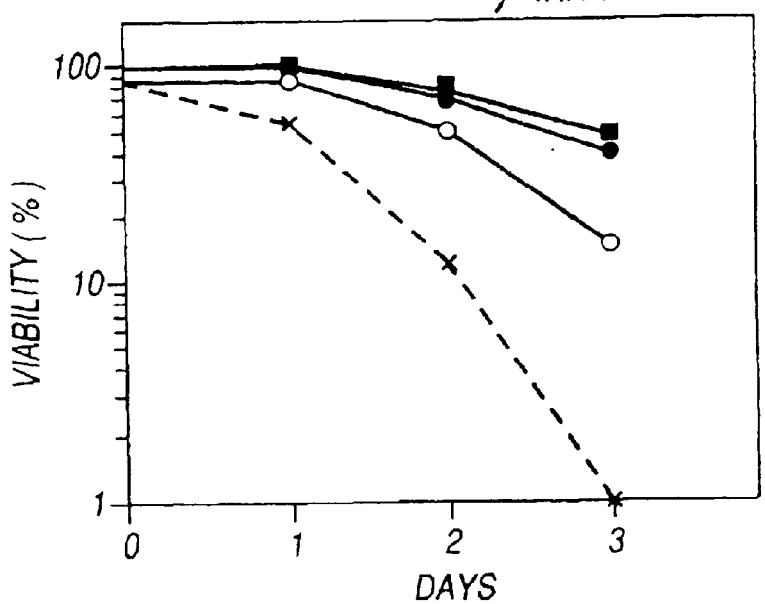

To ascertain whether Bcl-w enhanced or antagonised cell survival the transfected lines were subjected to various cytotoxic conditions. FDC-P1 cells expressing Bcl-w were notably more robust than the parental cells. Indeed, their survival after either IL-3 deprivation or γ-irradiation was comparable to that of lines over-expressing either Bcl-2 or Bcl-$x_L$ (FIG. 5A). Bcl-w also greatly enhanced the survival of the T hybridoma cells exposed to dexamethasone or irradiation (FIG. 5B). These results clearly place Bcl-w in the sub-family of Bcl-2-related proteins that inhibits cell death.

Figure 5C:
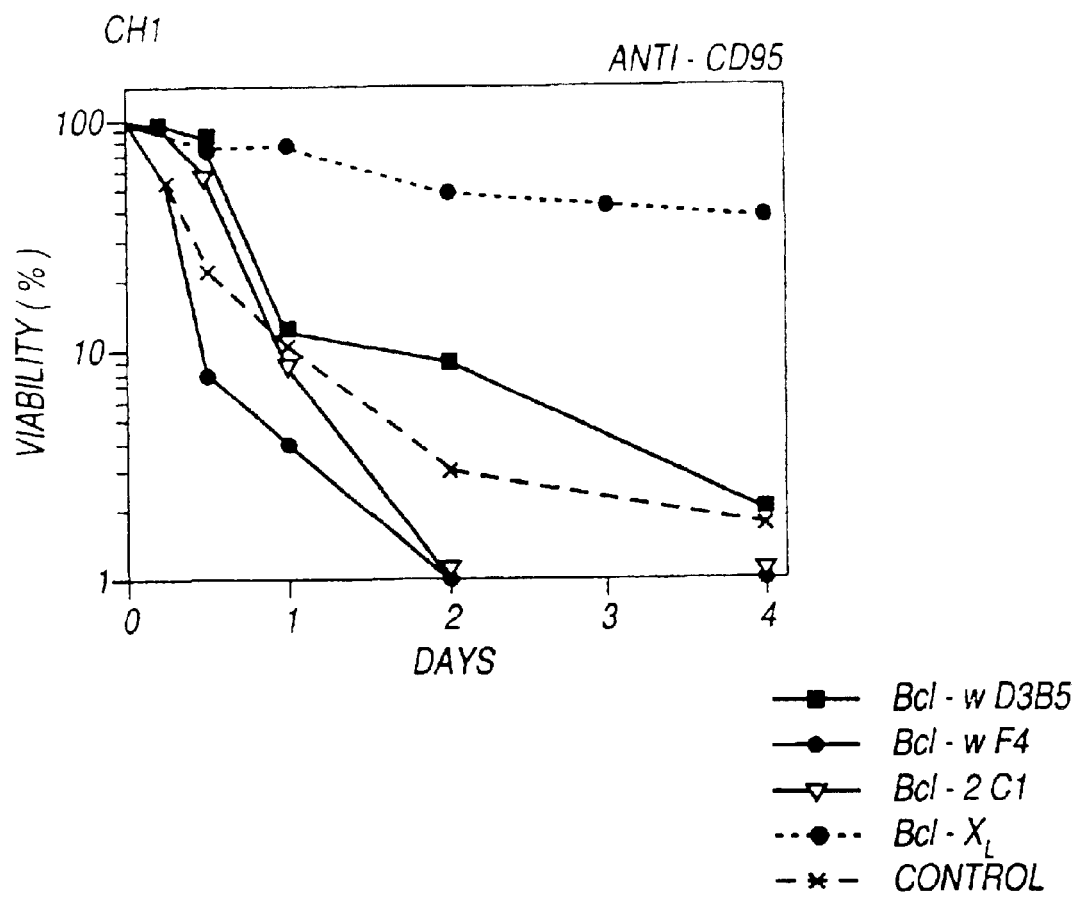
Figure 5C:
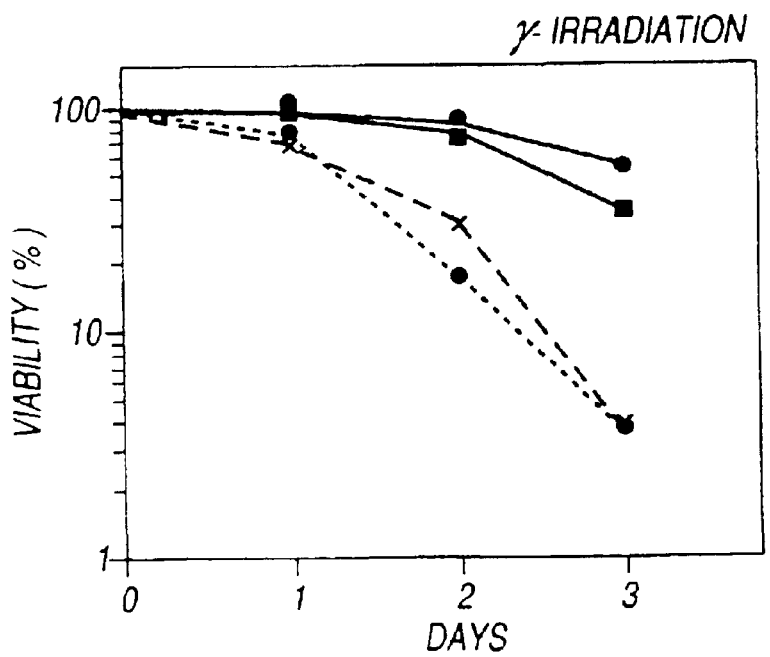

Bcl-2 and Bcl-$x_L$ are relatively ineffectual at protecting lymphoid cells against apoptosis induced by triggering the cell surface receptor CD9S, also known as Fas or APO-1 (Strasser et al, 1995). That also holds for Bcl-w. CH1 B lymphoma cells expressing levels of Bcl-w sufficient to protect against radiation-induced apoptosis (FIG. 5C, right panel) died as rapidly as control cells when incubated with anti-CD95 antibody Jo2 (FIG. 5C, left panel). In contrast, the cowpox virus protein CrmA, a potent inhibitor of the ICE cysteine protease (Ray et al., 1992), very effectively blocked apoptosis induced via CD95 (FIG. 5C, left panel) but failed to protect the cells from radiation-induced death (FIG. 5C, right panel). These results mean that apoptosis is induced by at least two pathways, only one of which involves activation of ICE.

EXAMPLE 9

Expression Pattern

Although bcl-2 and bcl-x are both widely expressed, their expression patterns differ significantly (Hockenbery et al., 1991; Krajewski et al., 1994). The expression patterns of bcl-x and bcl-w were compared by northern blot analysis of polyadenylated RNA. Both genes were expressed in many tissues and each gave highest levels in brain, colon and salivary gland (Table 3). Nevertheless, clear differences emerged upon analysis of a panel of haemopoietic cell lines (Table 4). While bcl-x RNA was detected in all 12 T lymphoid lines analysed and a few B lymphoid lines, bcl-w expression was rare in T and B lymphoid lines. Transcripts of both survival genes were, however, found in most of the 23 myeloid lines surveyed, which included lines of macrophage, megakaryocytic, erythroid and mast cell origin. Four lines having relatively high levels of bcl-w RNA were analysed by western blotting with polyclonal anti-Bcl-w antiserum and each contained the expected 22 kD protein (FIG. 4C). These findings establish that the expression pattern of bcl-w differs from that of bcl-x and raise the possibility that, within the haemopoietic system, bcl-w regulates survival in myeloid rather than lymphoid cells. In summary, he bcl-w gene is expressed in many cell types, and amongst the tissues surveyed, the Level was highest in brain, colon and salivary gland. A survey of 50 mouse haemopoietic cell lines revealed that bcl-w expression was common in cells of several myeloid lineages, including macrophage, megakaryocyte, erythroid and mast cell lines, but rare in either B or T lymphoid lines.

EXAMPLE 10

Localisation of the Human and Mouse bcl-w Genes

The chromosomal location of bcl-w in mice was determined genetically by exploiting an interspecific backcross panel that has been typed for over 2000 loci, well distributed over all the autosomes as well as the X chromosome (Copeland and Jenkins, 1991). Southern blots performed with a bcl-w probe on DNA from progeny derived from matings of {(C57BL/6J×Mus spretus)F$_1$×C57BL/6J} mice indicated that bcl-w resides in the central region of mouse chromosome 14 linked to surfactant-associated protein 1 (Sftp1), T-cell receptor alpha chain (Tcrα), and gap junction membrane channel protein alpha-3 (Gjα3). At least 134 mice were analysed for every marker, as shown in the segregation analysis (FIG. 6) and up to 183 mice were typed for some pairs of markers. The full data for each pairwise combination of markers were used to calculate recombination frequencies. For each pair of loci, the ratio of the number of mice exhibiting recombinant chromosomes to the number of mice analysed and the most likely gene order are: centromere-Sftp1-14/183-Tcrα-1/182-Bcl-w-1/147-Gjα3. The recombination frequencies, expressed in centiMorgans (cM), ± the standard error are: Sftp1-7.7±2.0-Tcrα-0.6±0.6-Bcl-w-0.7±0.7-Gjα3.

The central region of mouse chromosome 14 shares regions of homology with human chromosomes 10q, 14q and 13 (summarised in FIG. 6). In particular, Tcrα has been placed on human 14q11.2 and Gjα3 on 13. The tight linkage between Bcl-w, Tcrα and Gjα3 in the mouse suggested that Bcl-w would reside on either human 14q or 13. Fluorescence in situ hybridisation (FISH) analysis using a human cDNA from the coding region and a genomic probe spanning the intron between the coding exons clearly assigned bcl-w to human chromosome 14 at q11.2 (FIG. 7). Of the 20 metaphases scored for fluorescent signal using the intron probe, 15 showed signal on one or both chromatids of chromosome 14 in the region q11.2–q12 and 90% of the signal was at 14q11.2.

EXAMPLE 11

Method of Producing N-Terminal Fragment

Recombinant mouse Bcl-w polypeptide, tagged with an N-terminal FLAG epitope (DYKDDDK), was expressed in BL-21pLyS bacterial cells and purified on anti-FLAG antibody affinity matrix (Eastman-Kodak). The N-terminal 45 amino acids was determined using standard procedures following SDS-PAGE and electrotransfer on to the immobilising membrane PVDF (Ward et al, 1990). The first 27 amino acids were those corresponding to the FLAG epitope and the expected additional amino acids encoded by the expression vector. The next 18 amino acids corresponded to the N-terminal sequence of Bcl-w.

EXAMPLE 12

The nucleotide and corresponding amino acid sequence of human and murine bcl-w are shown in FIG. 9.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 3

TISSUE EXPRESSION OF bcl-w AND bcl-x (RNA)

| Tissue | bcl-w | bcl-x |
|---|---|---|
| brain | ++ | ++ |
| colon | ++ | ++ |
| salivary gland | ++ | ++ |
| liver | + | + |
| heart | + | +/- |
| stomach | + | + |
| muscle | + | +/- |
| testis | + | ++[g] |
| kidney | +/- | + |
| thymus | +/- | ++ |
| lymph node | - | - |
| placenta | + | ++ |
| fetal liver (d13-18) | - | - |

[g]larger size transcript

TABLE 4

EXPRESSION PATTERN OF bcl-w AND bcl-x IN CELL LINES

| CELL TYPE | bcl-w | bcl-x |
|---|---|---|
| B lymphoid | | |
| pre-B | 1/6 | 2/6[1] |
| B | 1/4 | 0/4[1] |
| | 2/10 | 2/10 |
| T lymphoid | | |
| DN | 3/4 | 4/4 |
| DP | 0/7 | 6/6 |
| SP | 1/2 | 2/2 |
| | 4/13 | 12/12 |
| Myeloid | | |
| macrophage | 14/19 | 16/16 |
| megakaryocyte | 2/2 | 2/2 |
| erythroid | 4/5 | 4/4 |
| mast | 1/1 | 1/1 |
| | 21/27 | 23/23 |

[1]marginal levels in all but 2 lines indicated

BIBLIOGRAPHY

Boise, L. H., Gonzalez-Garcia, M., Postema, C. E., Ding, L., Lindsten, T., Turka, L. A., Mao, X., Nunez, G. and Thompson, C. B. (1993). Cell, 74, 597–608.

Brand, S. F., Pichoff, S., Noselli S. and Bourbon, H. M. (1995). Gene, 154, 187–192.

Callen, D. F., Baker, E., Eyre, H. J., Chernos, J. E., Bell, J. A and Sutherland, G. R. (1990). Ann. Rev. Gen., 33, 219–221.

Chittenden, T., Flemington, C., Houghton, A. B., Ebb, R. G., Gallo, G. J., Elangovan, B., Chinnadurai G. and Lutz, R. J. (1995). EMBO J., 14, 5589–5596.

Copeland, N. G. and Jenkins, N. A. (1991). Trends Genet., 7, 113–118.

Cory, S. (1995). Ann. Rev. Immunol., 13, 513–543.

Dexter, T. M., Scott, G. D., Scolnick, E. and Metcalf, D. (1980). J. Exp. Med., 152,1036–1047.

Farrow, S. N., White, J. H. M., Martinou, I., Raven, T., Pun, K.-T., Grinham, C. J., Martinou, J.-C. and Brown, R. (1995). Nature, 374,731–733.

Green, E. L. (1981). Genetics and Probability in Animal Breeding Experiments. (eds). Oxford University Press New York, 77–113.

Haefliger, J.-A., Bruzzone, R., Jenkins, N. A., Gilbert, D. J., Copeland, N. G. and Paul, D. L. (1992). J. Biol. Chem., 267, 2057–2064.

Hockenbery, D. M., Zutter, M., Hickey, W., Nahm, M. and Korsmeyer, S. (1991). Proc. Natl. Acad. Sci. USA, 88, 6961–6965.

Hopp, T. P., Prickett, K. S., Price, V. L., Libby, R. T., March, C. J., Cerretti, D. P., Urdal, D. L. and Conlon, P. J. (1988). Biotechnology, 6, 1204–1210.

Jenkins, N. A., Copeland, N. G., Taylor, B. A. and Lee, B. K. (1982). J. Virol., 43, 26–36.

Kiefer, M. C., Brauer, M. J., Powers, V. C., Wu, J. J., Umansky, S. R., Tomei, L. D. and Barr, P. J. (1995). Nature, 374,736–739.

Krajewski, S., Krajewska, M., Shabaik, A, Wang, H. G., Irie, S., Fong, L. and Reed, J. C. (1994). Cancer Res., 54, 5501–5507.

Lynes, M. A, Lanier, L. L., Babcock, G. F., Wettstein, P. J. and Haughton, G. (1978). J. Immunol., 121, 2352–2357.

Mizushima, J. and Nagata, S. (1990). Nuc. Acids Res., 18, 5322.

Moore, K. J., D'Amore-Bruno, M. A., Korfhagen, T. R., Glasser, S. W., Whitsett, J. A., Jenkins, N. A. and Copeland, N. G. (1992). Genomics, 12, 388–393.

Nagata, S. and Golstein, P. (1995). Science, 267, 1449–1456.

Ogasawara J., Watanabe-Fukunaga, R., Adachi, M., Matsuzawa, A, Kasugai, T., Kitamura, Y., Itoh, N., Suda, T. and Nagata, S. (1993). Nature, 364, 806–809.

Oltvai, Z. N., Milliman, C. L. and Korsmeyer, S. J. (1993). Cell, 74, 609–619.

Ray, C. A., Black, R. A., Kronheim, S. R., Greenstreet, G. S. and Pickup, D. J. (1992). Cell, 69, 597–604.

Strasser, Harris, A. W., Huang D. C. S., Krammer, P. H. and Cory S. (1995) EMBO J, 14, 6136–6147.

Subramanian, T., Boyd, J. M. and Chinnadurai, G. (1995). Oncogene, 11, 2403–2409.

Teh, H.-S., Kishi, H., Scott, B. and von Boehmer, H. (1989). J. Exp. Med., 169, 795–806.

Visvader, J. E., Elefanty, A. G., Strasser, A. and Adams, J. M. (1992). EMBO J., 11, 4557–4564.

Ward, L. D, Hong, J, Whitehead, R. H., and Simpson R. J., (1990). Electrophoresis, 11, 883–891.

Yin, X-M., Oltvai, Z. N. and Korsmeyer, S. J. (1994). Nature, 369, 321–323.

What is claimed is:

1. An isolated nucleic acid molecule, wherein said nucleic acid molecule encodes a protein comprising an amino acid sequence as set forth in SEQ ID NO: 7.

2. An isolated nucleic acid molecule, wherein said nucleic acid molecule encodes the amino acid sequence as set forth in SEQ ID NO: 9.

3. An isolated nucleic acid molecule wherein said nucleic acid molecule comprises the nucleotide sequence as set forth in SEQ ID NO: 6.

4. An isolated nucleic acid molecule wherein said nucleic acid molecule comprises the nucleotide sequence as set forth in SEQ ID NO: 8.

* * * * *

SEQUENCE LISTING

<160> NUMBER OF SEQ ID NOS: 15

<210> SEQ ID NO 1
<211> LENGTH: 33

```
<212> TYPE: DNA
<213> ORGANISM: Mouse
<220> FEATURE:
<221> NAME/KEY: modified_base
<222> LOCATION: 16
<223> OTHER INFORMATION: n is inosine
<220> FEATURE:
<221> NAME/KEY: modified_base
<222> LOCATION: 19
<223> OTHER INFORMATION: n is inosine
<220> FEATURE:
<221> NAME/KEY: modified_base
<222> LOCATION: 22
<223> OTHER INFORMATION: n is inosine
<220> FEATURE:
<221> NAME/KEY: modified_base
<222> LOCATION: 25
<223> OTHER INFORMATION: n is inosine

<400> SEQUENCE: 1
gctctagaac tggggnhgnr tngtngcctt ytt                           33

<210> SEQ ID NO 2
<211> LENGTH: 9
<212> TYPE: PRT
<213> ORGANISM: Mouse
<220> FEATURE:
<221> NAME/KEY: Unsure
<222> LOCATION: 5
<223> OTHER INFORMATION: Xaa is Ile or Val

<400> SEQUENCE: 2

Asn Trp Gly Arg Xaa Val Ala Phe Phe
 1               5

<210> SEQ ID NO 3
<211> LENGTH: 31
<212> TYPE: DNA
<213> ORGANISM: Mouse
<220> FEATURE:
<221> NAME/KEY: modified_base
<222> LOCATION: 14
<223> OTHER INFORMATION: n is inosine
<220> FEATURE:
<221> NAME/KEY: modified_base
<222> LOCATION: 17
<223> OTHER INFORMATION: n is inosine
<220> FEATURE:
<221> NAME/KEY: modified_base
<222> LOCATION: 20
<223> OTHER INFORMATION: n is inosine

<400> SEQUENCE: 3
ggaattccca gccnccntkn tcttggatcc a                             31

<210> SEQ ID NO 4
<211> LENGTH: 8
<212> TYPE: PRT
<213> ORGANISM: Mouse
<220> FEATURE:
<221> NAME/KEY: Unsure
<222> LOCATION: 4
<223> OTHER INFORMATION: Xaa is Asp or Glu
<220> FEATURE:
<221> NAME/KEY: Unsure
<222> LOCATION: 5
<223> OTHER INFORMATION: Xaa is Asn or Gln

<400> SEQUENCE: 4

Trp Ile Gln Xaa Xaa Gly Gly Trp
 1               5
```

```
<210> SEQ ID NO 5
<211> LENGTH: 14
<212> TYPE: PRT
<213> ORGANISM: Mouse

<400> SEQUENCE: 5

Met Ala Thr Pro Ala Ser Thr Pro Asp Thr Arg Ala Leu Val
 1               5                  10

<210> SEQ ID NO 6
<211> LENGTH: 583
<212> TYPE: DNA
<213> ORGANISM: HUMAN
<220> FEATURE:
<221> NAME/KEY: CDS
<222> LOCATION: (1)..(579)

<400> SEQUENCE: 6 atg gcg acc cca gcc tcg gcc cca gac aca cgg gct ctg gtg gca gac       48
Met Ala Thr Pro Ala Ser Ala Pro Asp Thr Arg Ala Leu Val Ala Asp
 1               5                  10                  15 ttt gta ggt tat aag ctg agg cag aag ggt tat gtc tgt gga gct ggc       96
Phe Val Gly Tyr Lys Leu Arg Gln Lys Gly Tyr Val Cys Gly Ala Gly
             20                  25                  30 ccc ggg gag ggc cca gca gct gac ccg ctg cac caa gcc atg cgg gca      144
Pro Gly Glu Gly Pro Ala Ala Asp Pro Leu His Gln Ala Met Arg Ala
         35                  40                  45 gct gga gat gag ttc gag acc cgc ttc cgg cgc acc ttc tct gat ctg      192
Ala Gly Asp Glu Phe Glu Thr Arg Phe Arg Arg Thr Phe Ser Asp Leu
 50                  55                  60 gcg gct cag ctg cat gtg acc cca ggc tca gcc cag caa cgc ttc acc      240
Ala Ala Gln Leu His Val Thr Pro Gly Ser Ala Gln Gln Arg Phe Thr
 65                  70                  75                  80 cag gtc tcc gac gaa ctt ttt caa ggg ggc ccc aac tgg ggc cgc ctt      288
Gln Val Ser Asp Glu Leu Phe Gln Gly Gly Pro Asn Trp Gly Arg Leu
                 85                  90                  95 gta gcc ttc ttt ctc ttt ggg gct gca ctg tgt gct gag agt gtc aac      336
Val Ala Phe Phe Leu Phe Gly Ala Ala Leu Cys Ala Glu Ser Val Asn
            100                 105                 110 aag gag atg gaa cca ctg gtg gga caa gtg cag gag tgg atg gtg gcc      384
Lys Glu Met Glu Pro Leu Val Gly Gln Val Gln Glu Trp Met Val Ala
        115                 120                 125 tac ctg gag acg cgg ctg gtc gac tgg atc cac agc agt ggg ggc tgg      432
Tyr Leu Glu Thr Arg Leu Val Asp Trp Ile His Ser Ser Gly Gly Trp
    130                 135                 140 gcg gag ttc aca gct cta tac ggg gac ggg gcc ctg gag gag gcg cgg      480
Ala Glu Phe Thr Ala Leu Tyr Gly Asp Gly Ala Leu Glu Glu Ala Arg
145                 150                 155                 160 cgt ctg cgg gag ggg aac tgg gca tca gtg agg aca gtg ctg acg ggg      528
Arg Leu Arg Glu Gly Asn Trp Ala Ser Val Arg Thr Val Leu Thr Gly
                165                 170                 175 gcc gtg gca ctg ggg gcc ctg gta act gta ggg gcc ttt ttt gct agc      576
Ala Val Ala Leu Gly Ala Leu Val Thr Val Gly Ala Phe Phe Ala Ser
            180                 185                 190 aag tgaa                                                              583
Lys

<210> SEQ ID NO 7
<211> LENGTH: 193
<212> TYPE: PRT
<213> ORGANISM: HUMAN
```

-continued

```
<400> SEQUENCE: 7

Met Ala Thr Pro Ala Ser Ala Pro Asp Thr Arg Ala Leu Val Ala Asp
 1               5                  10                  15

Phe Val Gly Tyr Lys Leu Arg Gln Lys Gly Tyr Val Cys Gly Ala Gly
                20                  25                  30

Pro Gly Glu Gly Pro Ala Ala Asp Pro Leu His Gln Ala Met Arg Ala
            35                  40                  45

Ala Gly Asp Glu Phe Glu Thr Arg Phe Arg Arg Thr Phe Ser Asp Leu
 50                  55                  60

Ala Ala Gln Leu His Val Thr Pro Gly Ser Ala Gln Gln Arg Phe Thr
 65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
                100                 105                 110

Lys Glu Met Glu Pro Leu Val Gly Gln Val Gln Glu Trp Met Val Ala
            115                 120                 125

Tyr Leu Glu Thr Arg Leu Ala Asp Trp Ile His Ser Ser Gly Gly Trp
130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys
```

<210> SEQ ID NO 8
<211> LENGTH: 581
<212> TYPE: DNA
<213> ORGANISM: Mouse
<220> FEATURE:
<221> NAME/KEY: CDS
<222> LOCATION: (1)..(579)

```
<400> SEQUENCE: 8 atg ccg acc cca gcc tca acc cca gac aca cgc gct cta gtg gct gac      48
Met Pro Thr Pro Ala Ser Thr Pro Asp Thr Arg Ala Leu Val Ala Asp
 1               5                  10                  15 ttt gta ggc tat agg ctg agg cag aag ggt tat gtc tgt gga gct ggg      96
Phe Val Gly Tyr Arg Leu Arg Gln Lys Gly Tyr Val Cys Gly Ala Gly
                20                  25                  30 cct ggg gaa ggc cca gcc gcc gac ccg ctg cac caa gcc atg cgg gct     144
Pro Gly Glu Gly Pro Ala Ala Asp Pro Leu His Gln Ala Met Arg Ala
            35                  40                  45 gct gga gac gag ttt gag acc cgt ttc cgc cgc acc ttc tct gac ctg     192
Ala Gly Asp Glu Phe Glu Thr Arg Phe Arg Arg Thr Phe Ser Asp Leu
 50                  55                  60 gcc gct cag cta cac gtg acc cca ggc tca gcc cag caa cgc ttc acc     240
Ala Ala Gln Leu His Val Thr Pro Gly Ser Ala Gln Gln Arg Phe Thr
 65                  70                  75                  80 cag gtt tcc gac gaa ctt ttc caa ggg ggc cct aac tgg ggc cgt ctt     288
Gln Val Ser Asp Glu Leu Phe Gln Gly Gly Pro Asn Trp Gly Arg Leu
                85                  90                  95 gtg gca ttc ttt gtc ttt ggg gct gcc ctg tgt gct gag agt gtc aac     336
Val Ala Phe Phe Val Phe Gly Ala Ala Leu Cys Ala Glu Ser Val Asn
                100                 105                 110
```

-continued

```
aaa gaa atg gag cct ttg gtg gga caa gtc cag gat tgg atc gtg gcc      384
Lys Glu Met Glu Pro Leu Val Gly Gln Val Gln Asp Trp Ile Val Ala
        115                 120                 125 tac ctg gag aca cgt ctg gct gac tgg atc cac agc agt ggc ggc tgg      432
Tyr Leu Glu Thr Arg Leu Ala Asp Trp Ile His Ser Ser Gly Gly Trp
130                 135                 140 gcg gac ttc aca gct cta tac ggg gac ggg gcc ctg gag gac gca cgg      480
Ala Asp Phe Thr Ala Leu Tyr Gly Asp Gly Ala Leu Glu Asp Ala Arg
145                 150                 155                 160 cgt ctg cgg gag ggc aac tgg gca tga gtg agc aca gtg gtg acg ggg      528
Arg Leu Arg Glu Gly Asn Trp Ala Val Ser Thr Val Val Thr Gly Ala
                165                 170                 175 gcc gtg gca ctg ggg gcc ctg gta act gta ggg gcc ttt ttt gct agc      576
Val Ala Leu Gly Ala Leu Val Thr Val Gly Ala Phe Phe Ala Ser Lys
            180                 185                 190 aag tg                                                               581
```

<210> SEQ ID NO 9
<211> LENGTH: 193
<212> TYPE: PRT
<213> ORGANISM: Mouse

<400> SEQUENCE: 9

```
Met Ala Thr Pro Ala Ser Thr Pro Asp Thr Arg Ala Leu Val Ala Asp
  1               5                  10                  15

Phe Val Gly Tyr Lys Leu Arg Gln Lys Gly Tyr Val Cys Gly Ala Gly
                20                  25                  30

Pro Gly Glu Gly Pro Ala Ala Asp Pro Leu His Gln Ala Met Arg Ala
            35                  40                  45

Ala Gly Asp Glu Phe Glu Thr Arg Phe Arg Arg Thr Phe Ser Asp Leu
        50                  55                  60

Ala Ala Gln Leu His Val Thr Pro Gly Ser Ala Gln Gln Arg Phe Thr
    65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
                100                 105                 110

Lys Glu Met Glu Pro Leu Val Gly Gln Val Gln Asp Trp Met Val Ala
            115                 120                 125

Tyr Leu Glu Thr Arg Leu Ala Asp Trp Ile His Ser Ser Gly Gly Trp
        130                 135                 140

Ala Glu Phe Thr Ala Leu Tyr Gly Asp Gly Ala Leu Glu Glu Ala Arg
    145                 150                 155                 160

Arg Leu Arg Glu Gly Asn Trp Ala Ser Val Arg Thr Val Leu Thr Gly
                    165                 170                 175

Ala Val Ala Leu Gly Ala Leu Val Thr Val Gly Ala Phe Phe Ala Ser
                180                 185                 190

Lys
```

<210> SEQ ID NO 10
<211> LENGTH: 333
<212> TYPE: PRT
<213> ORGANISM: murine

<400> SEQUENCE: 10

```
Met Ala Thr Pro Ala Ser Thr Pro Asp Thr Arg Ala Leu Val Ala Asp
  1               5                  10                  15
```

```
Phe Val Gly Tyr Lys Leu Arg Gln Lys Gly Tyr Val Cys Gly Ala Gly
                20                  25                  30

Pro Gly Glu Gly Pro Ala Ala Asp Pro Leu His Gln Ala Met Arg Ala
            35                  40                  45

Ala Gly Asp Glu Phe Glu Thr Arg Phe Arg Arg Thr Phe Ser Asp Leu
     50                  55                  60

Ala Ala Gln Leu His Val Thr Pro Gly Ser Ala Gln Gln Arg Phe Thr
 65                  70                  75                  80

Gln Val Ser Asp Glu Leu Phe Gln Gly Pro Asn Trp Gly Arg Leu
                85                  90                  95

Val Ala Phe Phe Val Phe Gly Ala Ala Leu Cys Ala Glu Ser Val Asn
                100                 105                 110

Lys Glu Met Glu Pro Leu Val Gly Gln Val Gln Asp Trp Met Val Ala
            115                 120                 125

Tyr Leu Glu Thr Arg Leu Ala Asp Trp Ile His Ser Ser Gly Gly Trp
130                 135                 140

Glu Leu Glu Ala Ile Lys Ala Arg Val Arg Glu Met Glu Glu Glu Ala
145                 150                 155                 160

Glu Lys Leu Lys Glu Leu Gln Asn Glu Val Glu Lys Gln Met Asn Met
                165                 170                 175

Ser Pro Pro Gly Asn Ala Gly Pro Val Ile Met Ser Leu Glu Glu
            180                 185                 190

Lys Met Glu Ala Asp Ala Arg Ser Ile Tyr Val Gly Asn Val Asp Tyr
            195                 200                 205

Gly Ala Thr Ala Glu Glu Leu Glu Ala His Phe His Gly Cys Gly Ser
        210                 215                 220

Val Asn Arg Val Thr Ile Leu Cys Asp Lys Phe Ser Gly His Pro Lys
225                 230                 235                 240

Gly Phe Ala Tyr Ile Glu Phe Ser Asp Lys Glu Ser Val Arg Thr Ser
                245                 250                 255

Leu Ala Leu Asp Glu Ser Leu Phe Arg Gly Arg Gln Ile Lys Val Ile
                260                 265                 270

Pro Lys Arg Thr Asn Arg Pro Gly Ile Ser Thr Thr Asp Arg Gly Phe
            275                 280                 285

Pro Arg Ser Arg Tyr Arg Ala Arg Thr Thr Asn Tyr Asn Ser Ser Arg
        290                 295                 300

Ser Arg Phe Tyr Ser Gly Phe Asn Ser Arg Pro Arg Gly Arg Ile Tyr
305                 310                 315                 320

Arg Gly Arg Ala Arg Ala Thr Ser Trp Tyr Ser Pro Tyr
                325                 330

<210> SEQ ID NO 11
<211> LENGTH: 239
<212> TYPE: PRT
<213> ORGANISM: Homo sapiens

<400> SEQUENCE: 11

Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Thr Ala Ala Ser Arg Asp
     50                  55                  60
```

-continued

```
Pro Val Ala Arg Thr Ser Pro Leu Gln Thr Pro Ala Ala Pro Gly Ala
 65                  70                  75                  80

Ala Ala Gly Pro Ala Leu Ser Pro Val Pro Pro Val Val His Leu Thr
                 85                  90                  95

Leu Arg Gln Ala Gly Asp Asp Phe Ser Arg Arg Tyr Arg Arg Asp Phe
            100                 105                 110

Ala Glu Met Ser Arg Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 12
<211> LENGTH: 233
<212> TYPE: PRT
<213> ORGANISM: Homo sapiens

<400> SEQUENCE: 12

Met Ser Gln Ser Asn Arg Glu Leu Val Val Asp Phe Leu Ser Tyr Lys
  1               5                  10                  15

Leu Ser Gln Lys Gly Tyr Ser Trp Ser Gln Phe Ser Asp Val Glu Glu
                 20                  25                  30

Asn Arg Thr Glu Ala Pro Glu Gly Thr Glu Ser Glu Met Glu Thr Pro
             35                  40                  45

Ser Ala Ile Asn Gly Asn Pro Ser Trp His Leu Ala Asp Ser Pro Ala
         50                  55                  60

Val Asn Gly Ala Thr Gly His Ser Ser Ser Leu Asp Ala Arg Glu Val
 65                  70                  75                  80

Ile Pro Met Ala Ala Val Lys Gln Ala Leu Arg Glu Ala Gly Asp Glu
                 85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
```

-continued

```
                195                 200                 205
Arg Phe Asn Arg Trp Phe Leu Thr Gly Met Thr Val Ala Gly Val Val
    210                 215                 220
Leu Leu Gly Ser Leu Phe Ser Arg Lys
225                 230

<210> SEQ ID NO 13
<211> LENGTH: 211
<212> TYPE: PRT
<213> ORGANISM: Homo sapiens

<400> SEQUENCE: 13

Met Ala Ser Gly Gln Gly Pro Gly Pro Pro Arg Gln Glu Cys Gly Glu
 1               5                  10                  15
Pro Ala Leu Pro Ser Ala Ser Glu Glu Gln Val Ala Gln Asp Thr Glu
                20                  25                  30
Glu Val Phe Arg Ser Tyr Val Phe Tyr Arg His Gln Gln Glu Gln Glu
             35                  40                  45
Ala Glu Gly Val Ala Ala Pro Ala Asp Pro Glu Met Val Thr Leu Pro
         50                  55                  60
Leu Gln Pro Ser Ser Thr Met Gly Gln Val Gly Arg Gln Leu Ala Ile
65                  70                  75                  80
Ile Gly Asp Asp Ile Asn Arg Arg Tyr Asp Ser Glu Phe Gln Thr Met
                 85                  90                  95
Leu Gln His Leu Gln Pro Thr Ala Glu Asn Ala Tyr Glu Tyr Phe Thr
            100                 105                 110
Lys Ile Ala Thr Ser Leu Phe Glu Ser Gly Ile Asn Trp Gly Arg Val
        115                 120                 125
Val Ala Leu Leu Gly Phe Gly Tyr Arg Leu Ala Leu His Val Tyr Gln
    130                 135                 140
His Gly Leu Thr Gly Phe Leu Gly Gln Val Thr Arg Phe Val Val Asp
145                 150                 155                 160
Phe Met Leu His His Cys Ile Ala Arg Trp Ile Ala Gln Arg Gly Gly
                165                 170                 175
Trp Val Ala Ala Leu Asn Leu Gly Asn Gly Pro Ile Leu Asn Val Leu
            180                 185                 190
Val Val Leu Gly Val Val Leu Leu Gly Gln Phe Val Val Arg Arg Phe
        195                 200                 205
Phe Lys Ser
    210

<210> SEQ ID NO 14
<211> LENGTH: 192
<212> TYPE: PRT
<213> ORGANISM: Homo sapiens

<400> SEQUENCE: 14

Met Asp Gly Ser Gly Glu Gln Pro Arg Gly Gly Gly Pro Thr Ser Ser
 1               5                  10                  15
Glu Gln Ile Met Lys Thr Gly Ala Leu Leu Leu Gln Gly Phe Ile Gln
                20                  25                  30
Asp Arg Ala Gly Arg Met Gly Gly Glu Ala Pro Glu Leu Ala Leu Asp
             35                  40                  45
Pro Val Pro Gln Asp Ala Ser Thr Lys Lys Leu Ser Glu Cys Leu Lys
         50                  55                  60
Arg Ile Gly Asp Glu Leu Asp Ser Asn Met Glu Leu Gln Arg Met Ile
```

```
                    65                  70                  75                  80
Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
               100                 105                 110

Leu Phe Tyr Phe Ala Ser Lys Leu Val Leu Lys Ala Leu Cys Thr Lys
               115                 120                 125

Val Pro Glu Leu Ile Arg Thr Ile Met Gly Trp Thr Leu Asp Phe Leu
           130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
               165                 170                 175

Val Ala Gly Val Leu Thr Ala Ser Leu Thr Ile Trp Lys Lys Met Gly
               180                 185                 190

<210> SEQ ID NO 15
<211> LENGTH: 137
<212> TYPE: PRT
<213> ORGANISM: Homo sapiens

<400> SEQUENCE: 15

Asp Ile Glu Gly Phe Val Val Asp Tyr Phe Thr His Arg Ile Arg Gln
 1               5                  10                  15

Asn Gly Met Glu Trp His Glu Met Met Arg Val Met Gly Thr Ile Phe
                20                  25                  30

Glu Lys Lys His Ala Glu Asn Phe Glu Thr Phe Cys Glu Gln Leu Leu
            35                  40                  45

Ala Val Pro Arg Ile Ser Phe Ser Leu Tyr Gln Asp Val Val Arg Thr
        50                  55                  60

Val Gly Asn Ala Gln Thr Asp Gln Cys Pro Met Ser Tyr Gly Arg Leu
65                  70                  75                  80

Ile Gly Leu Ile Ser Phe Gly Gly Phe Val Ala Ala Lys Met Met Glu
                85                  90                  95

Ser Val Glu Leu Gln Gly Gln Val Arg Asn Leu Phe Val Tyr Thr Ser
               100                 105                 110

Leu Phe Ile Lys Thr Arg Ile Arg Asn Asn Trp Lys Glu His Asn Arg
           115                 120                 125

Ser Trp Asp Asp Phe Met Thr Leu Gly
       130                 135
```